(12) United States Patent
Kurono et al.

(10) Patent No.: US 9,541,567 B2
(45) Date of Patent: Jan. 10, 2017

(54) SAMPLE ANALYZER WITH LIQUID ASPIRATING UNIT AND LIQUID SURFACE DETECTOR

(75) Inventors: Hiroshi Kurono, Kobe (JP); Takashi Yamato, Kakogawa (JP)

(73) Assignee: SYSMEX CORPORATION, Kobe-shi (JP)

(*) Notice: Subject to any disclaimer, the term of this patent is extended or adjusted under 35 U.S.C. 154(b) by 1004 days.

(21) Appl. No.: 13/166,439

(22) Filed: Jun. 22, 2011

(65) Prior Publication Data

US 2011/0318845 A1    Dec. 29, 2011

(30) Foreign Application Priority Data

Jun. 24, 2010    (JP) ................. 2010-144066

(51) Int. Cl.
    *G01N 35/10*    (2006.01)
    *G01F 23/26*    (2006.01)
    *G01N 35/00*    (2006.01)

(52) U.S. Cl.
    CPC ...... *G01N 35/1009* (2013.01); *G01N 35/0092* (2013.01); *G01N 35/00732* (2013.01); *G01N 35/1002* (2013.01); *G01N 2035/1025* (2013.01); *Y10T 436/25* (2015.01)

(58) Field of Classification Search
    None
    See application file for complete search history.

(56) References Cited

U.S. PATENT DOCUMENTS

| | | | |
|---|---|---|---|
| 2003/0194349 A1* | 10/2003 | Carey | B01L 3/508 422/63 |
| 2009/0000401 A1* | 1/2009 | Oonuma | 73/864.11 |
| 2010/0104478 A1 | 4/2010 | Kondou | |
| 2010/0132438 A1* | 6/2010 | Burkard | 73/64.53 |

FOREIGN PATENT DOCUMENTS

| | | |
|---|---|---|
| JP | 06-066813 A1 | 3/1994 |
| JP | 2009-180605 A | 8/2009 |

* cited by examiner

*Primary Examiner* — Yelena G Gakh
*Assistant Examiner* — Michelle Adams
(74) *Attorney, Agent, or Firm* — Mots Law, PLLC

(57) ABSTRACT

A sample analyzer is configured to execute a liquid surface detection of detecting a liquid surface in a container by a liquid surface detector prior to a lowering operation of an aspirating tube for aspirating the liquid if a liquid level information is not stored in a memory, and store a liquid level information of a container in the memory based on a detection result by the liquid surface detection. Also, a liquid aspirating method by a sample analyzer.

10 Claims, 17 Drawing Sheets

| 501 | 502 | 503 | ... | 504 |
|---|---|---|---|---|
| CONTAINER RACK ID | HOLDER NUMBER | TYPE OF REAGENT | ... | LIQUID LEVEL INFORMATION |
| R001 | 1 | PT | ... | 110 |
| R001 | 2 | APTT | ... | |
| R003 | 5 | CALCIUM CHLORIDE | ... | 130 |
| ⋮ | ⋮ | ⋮ | ... | ⋮ |

| 601 | 602 | 603 | ... | 604 |
|---|---|---|---|---|
| CONTAINER RACK ID | HOLDER NUMBER | TYPE OF REAGENT | ... | LIQUID LEVEL STORAGE FLAG |
| R001 | 1 | PT | ... | 1 |
| R001 | 2 | APTT | ... | 0 |
| R003 | 5 | CALCIUM CHLORIDE | ... | 1 |
| ⋮ | ⋮ | ⋮ | ... | ⋮ |

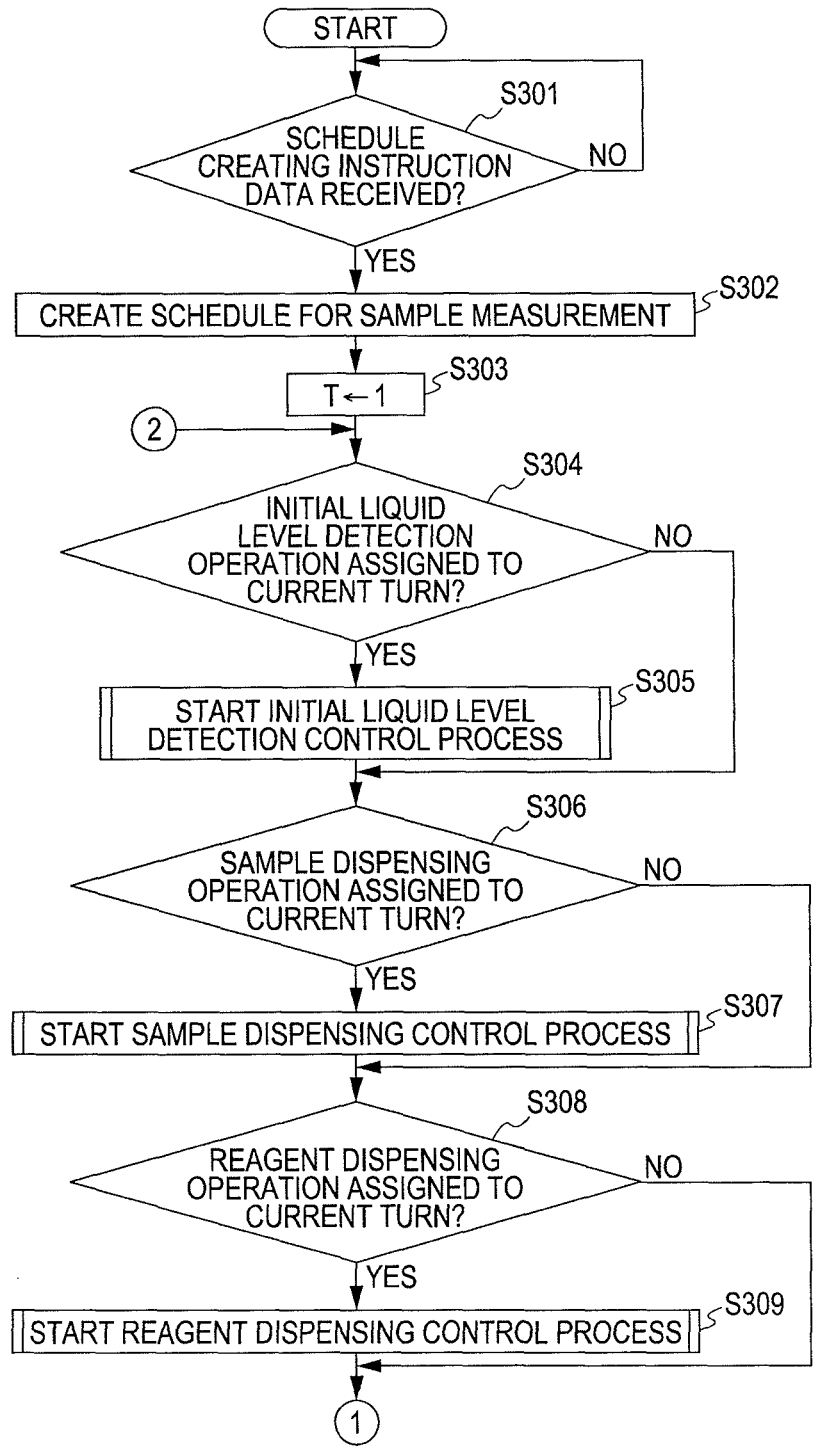

SAMPLE ANALYZER WITH LIQUID ASPIRATING UNIT AND LIQUID SURFACE DETECTOR

FIELD OF THE INVENTION

The present invention relates to a sample analyzer for analyzing samples such as blood and urine, and to a liquid aspirating method of aspirating liquid such as sample or reagent for sample analysis.

BACKGROUND

Conventionally, a sample analyzer for aspirating liquid by an aspirating tube from a container accommodating the liquid such as sample or reagent is known (see e.g., Japanese Laid-Open Patent Publication No. 2009-180605).

For the purpose of efficient reagent aspirating process, the sample analyzer disclosed in Japanese Laid-Open Patent Publication NO. 2009-180605 sets a lowering speed switching height for switching a speed of lowering a reagent aspirating nozzle by adding a margin value to a height of a reagent in a reagent bottle, lowers at high speed the reagent nozzle to the lowering speed switching height, and lowers at low speed the reagent nozzle from the lowering speed switching height to the reagent in the reagent bottle. In the sample analyzer disclosed in Japanese Laid-Open Patent Publication NO. 2009-180605, an initial liquid level of the reagent in the reagent bottle is stored in a memory in advance according to a type of the reagent bottle. Unless an aspiration of the reagent has been performed from the reagent bottle, the lowering speed switching height is set using the initial liquid level stored in the memory. Then the reagent nozzle is lowered at high speed to the set lowering speed switching height, and the reagent nozzle is lowered at low speed from the lowering speed switching height.

However, in the sample analyzer disclosed in Japanese Laid-Open Patent Publication No. 2009-180605, the size of the reagent bottle varies due to machining error of the reagent bottle or the like even with the same type of the reagent bottle, and thus an actual initial liquid level may differ from the initial liquid level stored in the memory and the reagent nozzle may enter into the reagent while lowering at high speed. To prevent this, the margin value used for a setting of the lowering speed switching height needs to be greatly ensured. As a result, the lowering speed switching height is set at a high position. Therefore, it may become difficult to perform a reagent aspirating operation rapidly.

In view of such aspects, it is a main object of the present invention to provide a sample analyzer and a liquid aspirating method enabling to perform a liquid aspirating operation more rapidly than the prior art when a liquid level is unknown.

SUMMARY OF THE INVENTION

The scope of the present invention is defined solely by the appended claims, and is not affected to any degree by the statements within this summary.

According to a first aspect of the present invention, a sample analyzer comprising:

a liquid aspirating unit that includes an aspirating tube and an actuator for moving the aspirating tube in an up and down direction, and that aspirates a liquid for a sample analysis using the aspirating tube from a container;

a liquid surface detector for detecting a liquid surface in the container;

a memory for storing a liquid level information indicating a liquid level in the container based on a detection result by the liquid surface detector; and a controller for controlling a speed for lowering the aspirating tube with respect to the liquid surface in the container by the actuator based on the liquid level information stored in the memory, and controlling the liquid aspirating unit to aspirate the liquid from the container with the aspirating tube, wherein the controller executes a liquid surface detection of detecting the liquid surface in the container by the liquid surface detector prior to a lowering operation of the aspirating tube for aspirating the liquid if the liquid level information is not stored in the memory, and stores a liquid level information of the container in the memory based on a detection result by the liquid surface detection.

According to a second aspect of the present invention, a liquid aspirating method by a sample analyzer including an aspirating tube for aspirating a liquid for a sample analysis from a container, and a memory for storing a liquid level information indicating a liquid level in the container, wherein the liquid aspirating method comprising steps of:

(i) if the liquid level information is stored in the memory, controlling a speed for lowering the aspirating tube with respect to the liquid surface in the container based on the liquid level information stored in the memory and aspirating the liquid from the container with the aspirating tube; and (ii) if the liquid level information is not stored in the memory, (a) executing a liquid surface detection of detecting the liquid surface in the container prior to a lowering operation of the aspirating tube for aspirating the liquid, and (b) storing the liquid level information of the container in the memory based on a detection result by the liquid surface detection.

BRIEF DESCRIPTION OF THE DRAWINGS

FIG. 8A is a schematic view showing a configuration of a first reagent information database;

FIG. 8B is a schematic view showing a configuration of a second reagent information database;

FIG. 10B is a flowchart (first half) showing the processing procedure of the CPU of the measurement device in the sample analyzing operation;

DETAILED DESCRIPTION OF THE PREFERRED EMBODIMENTS

The preferred embodiments of the present invention will be described below with reference to the drawings.

[Configuration of Sample Analyzer]

Figure 1:
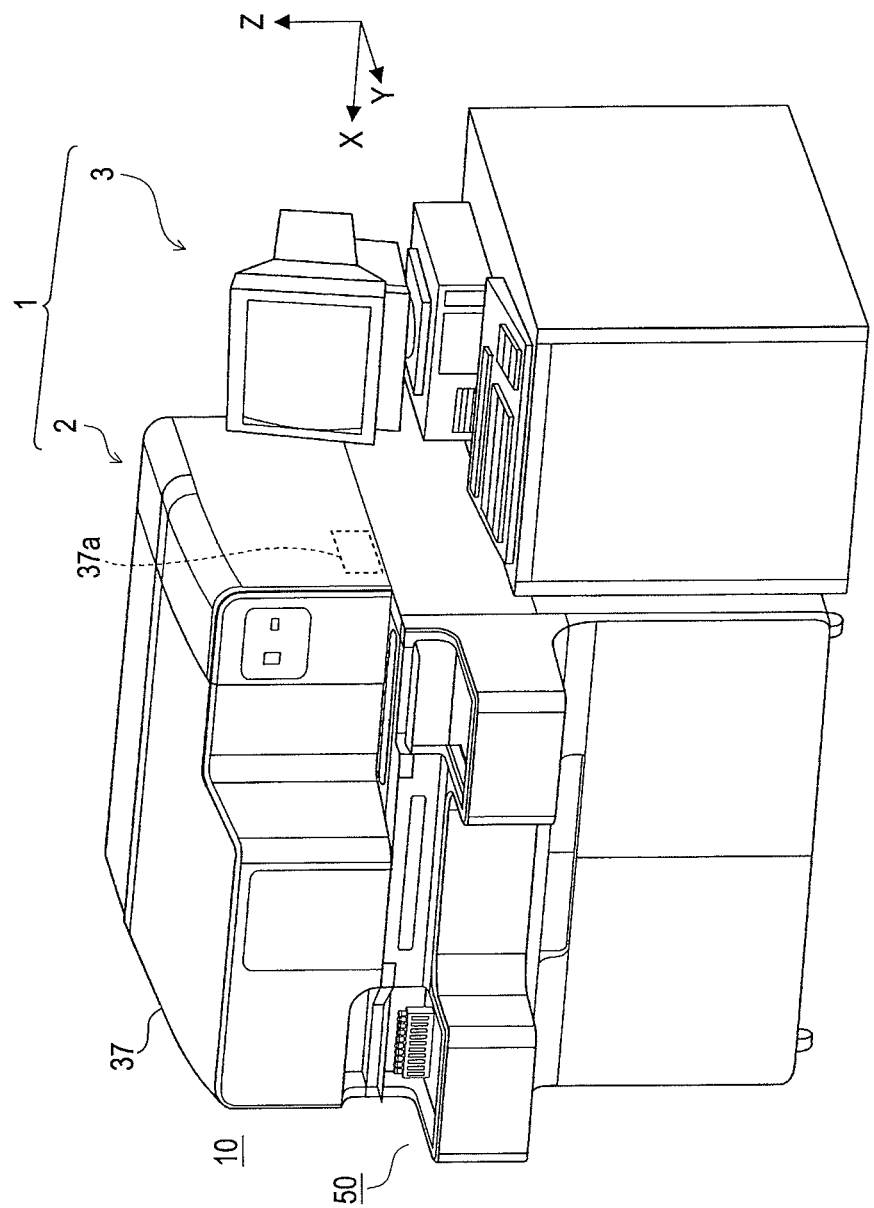
FIG. 1 is a perspective view showing a configuration of a sample analyzer according to the present embodiment.

FIG. 1 is a perspective view showing a configuration of a sample analyzer 1 according to the present embodiment. The sample analyzer 1 is configured by a measurement device 2 for optically measuring a component contained in a sample (blood), and an information processing device 3 for analyzing the measurement data by the measurement device 2 and giving an operation instruction to the measurement device 2.

Figure 2:
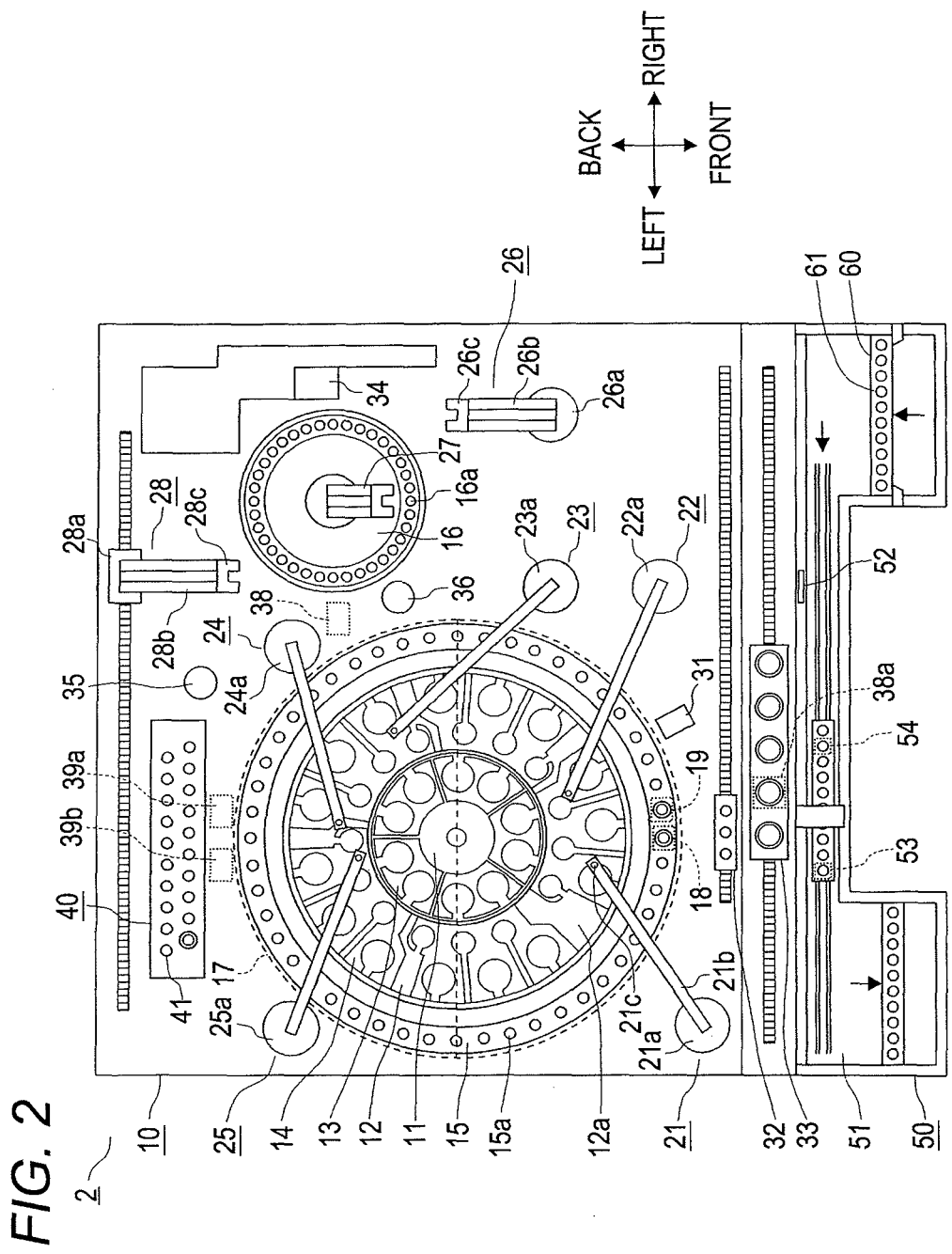
FIG. 2 is a plan view showing a schematic configuration of the interior of a measurement device when viewed from an upward direction.

FIG. 2 is a plan view showing a schematic configuration of the interior of the measurement device 2 when viewed from an upward direction. The measurement device 2 is configured by a measurement unit 10, a detection unit 40, and a transport unit 50.

The measurement unit 10 includes a first reagent table 11, a second reagent table 12, a first container rack 13, a second container rack 14, a cuvette table 15, a warming table 16, a table cover 17, a first sample dispensing unit 21, a second sample dispensing unit 22, a first reagent dispensing unit 23, a second reagent dispensing unit 24, a third reagent dispensing unit 25, a first catcher unit 26, a second catcher unit 27, a third catcher unit 28, a reagent barcode reader 31, a cuvette transport unit 32, a diluted solution transport unit 33, a cuvette port 34, and discarding ports 35, 36.

As shown in FIG. 1, the measurement device 2 includes a cover 37. The cover 37 can be opened and closed, where the user can access the first reagent table 11, the second reagent table 12, the cuvette table 15, the warming table 16, the table cover 17, and the detection unit 40 by opening the cover 37. The cover 37 includes a lock mechanism 37a, so that the cover 37 can be locked with the lock mechanism 37a. That is, when the cover 37 is in the locked state, the access of the user to the first reagent table 11, the second reagent table 12, the cuvette table 15, the warming table 16, the table cover 17, and the detection unit 40 is prohibited.

The first reagent table 11, the second reagent table 12, the cuvette table 15, and the warming table 16 are circular tables, and are rotatably driven independently in both clockwise direction and counterclockwise direction. The rotational drive of such tables is carried out by a plurality of stepping motors (not shown) arranged on the back side of the lower surface.

As shown in the figure, five first container racks 13 and five second container racks 14 are removably arranged on the upper surface of the first reagent table 11 and the second reagent table 12, respectively. The first container rack 13 and the second container rack 14 are formed with a holder for holding the reagent container.

Figure 3A:
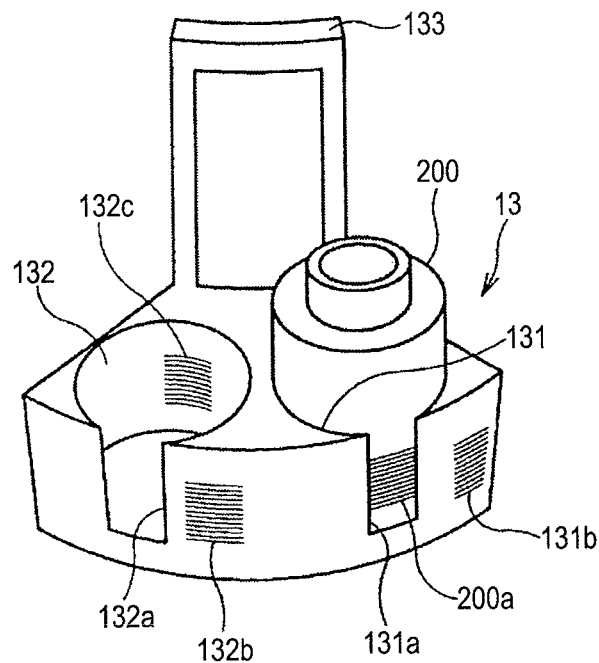
FIG. 3A is a perspective view showing a configuration of a first container rack.

FIG. 3A is a perspective view showing a configuration of the first container rack 13. The first container rack 13 includes two holders 131, 132 for holding a cylindrical reagent container 200, cutouts 131a, 132a arranged on the front surface side of the holders 131, 132, respectively, and a gripping portion 133 arranged to project to the upper side. The holders 131, 132 have the accommodating portion formed to a recess having a substantially circular shape in plan view to be able to hold to the reagent container 200.

The barcode labels 131b, 132b are attached to the outer peripheral surfaces of the holders 131, 132, respectively. The barcode label is also attached to the inner peripheral surface of the holder 131, 132. The barcode label 200a is attached to the reagent container 200. In the figure, only the barcode label 132c of the barcodes attached to the inner peripheral surface of the holders 131, 132 is shown.

Figure 3B:
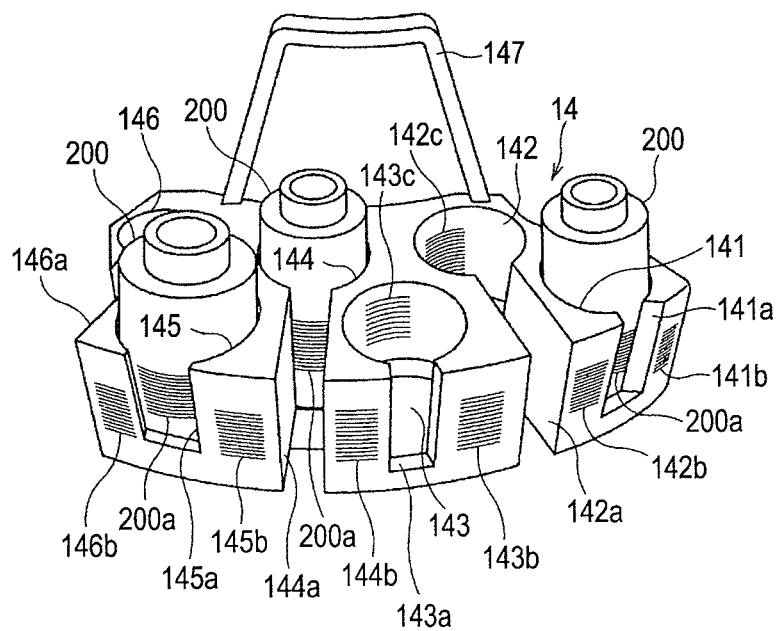
FIG. 3B is a perspective view showing a configuration of a second container rack.

FIG. 3B is a perspective view showing a configuration of the second container rack 14. The second container rack 14 includes six holders 141 to 146 for holding a cylindrical reagent container 200, cutouts 141a to 146a arranged on the front surface side of the holders 141 to 146, respectively, and a gripping portion 147 arranged to project to the upper side. The holders 141 to 146 have the accommodating portion formed to a recess having a substantially circular shape in plan view to be able to hold to the reagent container 200.

The barcode labels 141b to 146b are attached to the outer peripheral surfaces of the holders 141 to 146, respectively. The barcode label is also attached to the inner peripheral surface of the holder 141 to 146. The barcode label 200a is attached to the reagent container 200. In the figure, only the barcode labels 142c, 143c of the barcode labels attached to the inner peripheral surface of the holders 141 to 146 are shown.

When the barcode of the reagent held in the first reagent table 11 and the second reagent table 12 is read, the first reagent table 11 and the second reagent table 12 rotated in a predetermined direction and speed, so that the barcode of the barcode label attached to the outer peripheral surface of the holders of the first container rack 13 or the second container rack 14 is read by the barcode reader 31. Therefore, in which holder of which container rack the relevant holder is arranged can be recognized.

Thereafter, the barcode positioned at the cutout of the relevant holder is read. In this case, the barcode of the barcode label attached to the reagent container 200 is read if the reagent container 200 is accommodated, and the barcode of the barcode label attached to the inner peripheral surface of the holder is read if the reagent container 200 is not accommodated. Whether or not the reagent container 200 is held in the holder can be recognized in such manner. Furthermore, if the reagent container 200 is held in the holder, the type of reagent accommodated in the reagent container 200 is identified by the barcode information read from the barcode of the barcode label 200a. The holding position and the type of reagent obtained in such manner are stored in correspondence to each other.

Returning back to FIG. 2, the cuvette table 15 and the warming table 16 are respectively formed with a plurality of cuvette holding holes 15a1, 16a along the circumference, as shown in the figure. When the cuvette is set in the cuvette holding hole 15a1, 16a, the relevant cuvette moves through the circumference position in accordance with the rotation of the cuvette table 15 and the warming table 16, respectively. The warming table 16 warms the cuvette set in the holding hole 16a at a predetermined temperature.

The table cover 17 is arranged to cover the upper surfaces of the first reagent table 11, the second reagent table 12, and the cuvette table 15. The table cover 17 is configured to be bendable at the central portion so that only the first half of the first reagent table 11, the second reagent table 12, and the cuvette table 15 can be opened. The table cover 17 includes a plurality of holes (not shown). The first sample dispensing unit 21, the second sample dispensing unit 22, the first reagent dispensing unit 23, the second reagent dispensing unit 24, and the third reagent dispensing unit 25 dispense the reagent through the plurality of holes.

Figure 4:
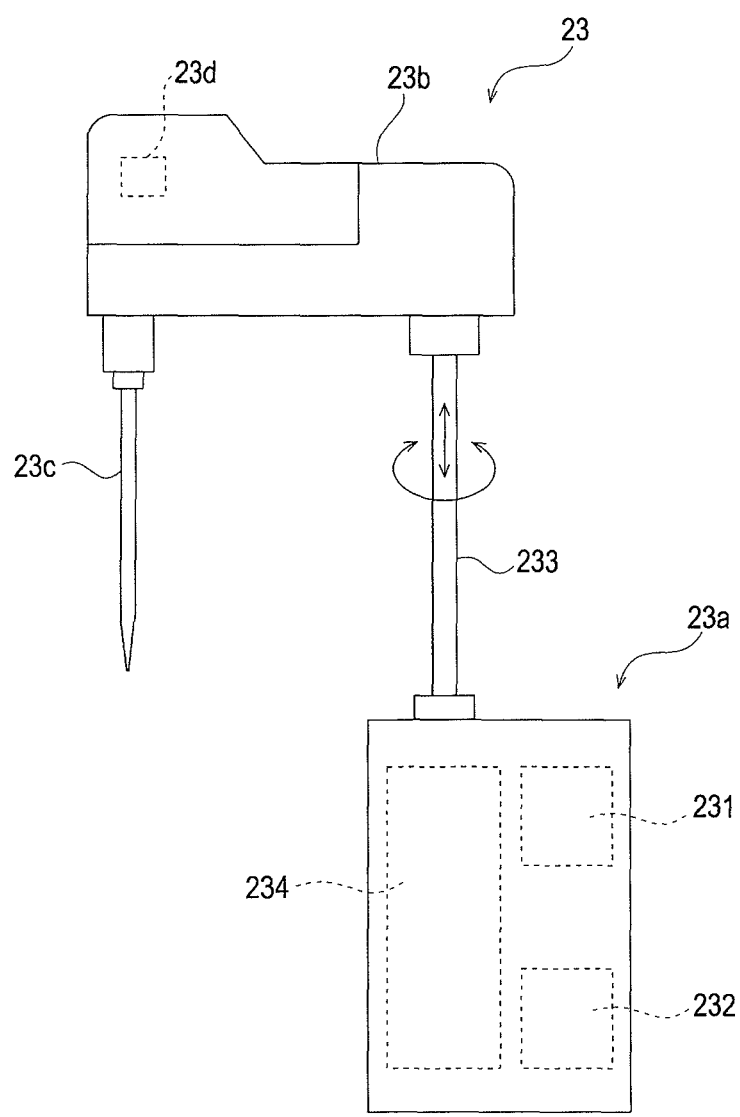
FIG. 4 is a side view showing a configuration of a first reagent dispensing unit.

FIG. 4 is a side view showing a configuration of the first reagent dispensing unit 23. As shown in the figure, the first reagent dispensing unit 23 includes a drive unit 23a, an arm 23b, and a pipette 23c. The drive unit 23a includes a rotation motor 231, a raising and lowering motor 232, and a transmission mechanism 234 for transmitting the power of the rotation motor 231 and the raising and lowering motor 232 to a shaft 233. The transmission mechanism 234 is configured by a belt transmission mechanism or a rack pinion mechanism for directly converting the rotation power of the raising and lowering motor 232 to a linear power in the up and down direction and transmitting to the shaft 233 such as a belt transmission mechanism or a gear mechanism for reducing the rotation power of the rotation motor 231 and transmitting to the shaft 233. The rotation direction and the rotation amount of the rotation motor 231 are detected by a rotary encoder 235, and the rotation direction and the rotation amount (i.e., up and down movement direction and movement amount of pipette 23c) of the raising and lowering motor 232 are detected by a rotary encoder 236.

A contact type capacitance sensor 23d for detecting that the distal end of the pipette 23c is contacting the liquid surface is connected to the pipette 23c of the first reagent dispensing unit 23. When the sample is aspirated by the pipette 23c, the pipette 23c is lowered and brought into contact with the liquid surface of the sample, and the detection signal is output from the capacitance sensor 23d.

The configurations of the first sample dispensing unit 21, the second sample dispensing unit 22, the second reagent dispensing unit 24, and the third reagent dispensing unit 25 are similar to the configuration of the first reagent dispensing unit 23, and thus the description will be omitted.

Returning back to FIG. 2, the first catcher unit 26 is configured by a supporting portion 26a for supporting an arm 26b, an extendable arm 26b, and a grip portion 26c. The supporting portion 26a is rotatably driven by a stepping motor 315a (see FIG. 5) arranged on the back side of the lower surface. The grip portion 26c is attached to the distal end of the arm 26b and can grip the cuvette. The second catcher unit 27 has a configuration similar to the first catcher unit 26, and is rotated by the stepping motor 315b (see FIG. 5).

The third catcher unit 28 is configured by a supporting portion 28a for supporting an arm 28b, an extendable arm 28b, and a grip portion 28c attached to the distal end of the arm 28b, as shown in the figure. The supporting portion 28a is driven along a rail arranged in the left and right direction. The grip portion 28c can grip the cuvette.

The reagent barcode reader 31 reads the barcode labels attached to the first container rack 13 and the second container rack 14, and the barcode label 200a attached to the reagent container 200 accommodated in such racks.

The cuvette transport unit 32 and the diluted solution transport unit 33 are driven on the rail in the left and right direction. The cuvette transport unit 32 and the diluted solution transport unit 33 respectively includes a hole for holding the cuvette and the diluted solution container.

A new cuvette is always supplied to the cuvette port 34. The new cuvette is set in the hole for holding the cuvette of the cuvette transport unit 32 and the cuvette holding hole 15a of the cuvette table 15 by the first catcher unit 26 and the second catcher unit 27. The discarding ports 351, 36 are holes for discarding the cuvettes which analysis is terminated and is no longer necessary.

The detection unit 40 includes 20 holding holes 41 for accommodating the cuvette at the upper surface, and includes a detection unit (not shown) on the back side of the lower surface. When the cuvette is set in the holding hole 41, the optical information is detected by the detection unit from the measurement specimen in the cuvette.

The transport unit 50 includes a transport path 51 and a sample barcode reader 52. The bottom surface of the transport path 51 includes a pre-analysis rack holding region on the right side, a transport region at the middle, and a post-analysis rack holding region on the left side, and is formed to a horseshoe shape. The sample barcode reader 52 reads the barcode of the barcode label attached to the sample container 61 accommodated in the sample rack 60 transported through the transport region.

Figure 5:
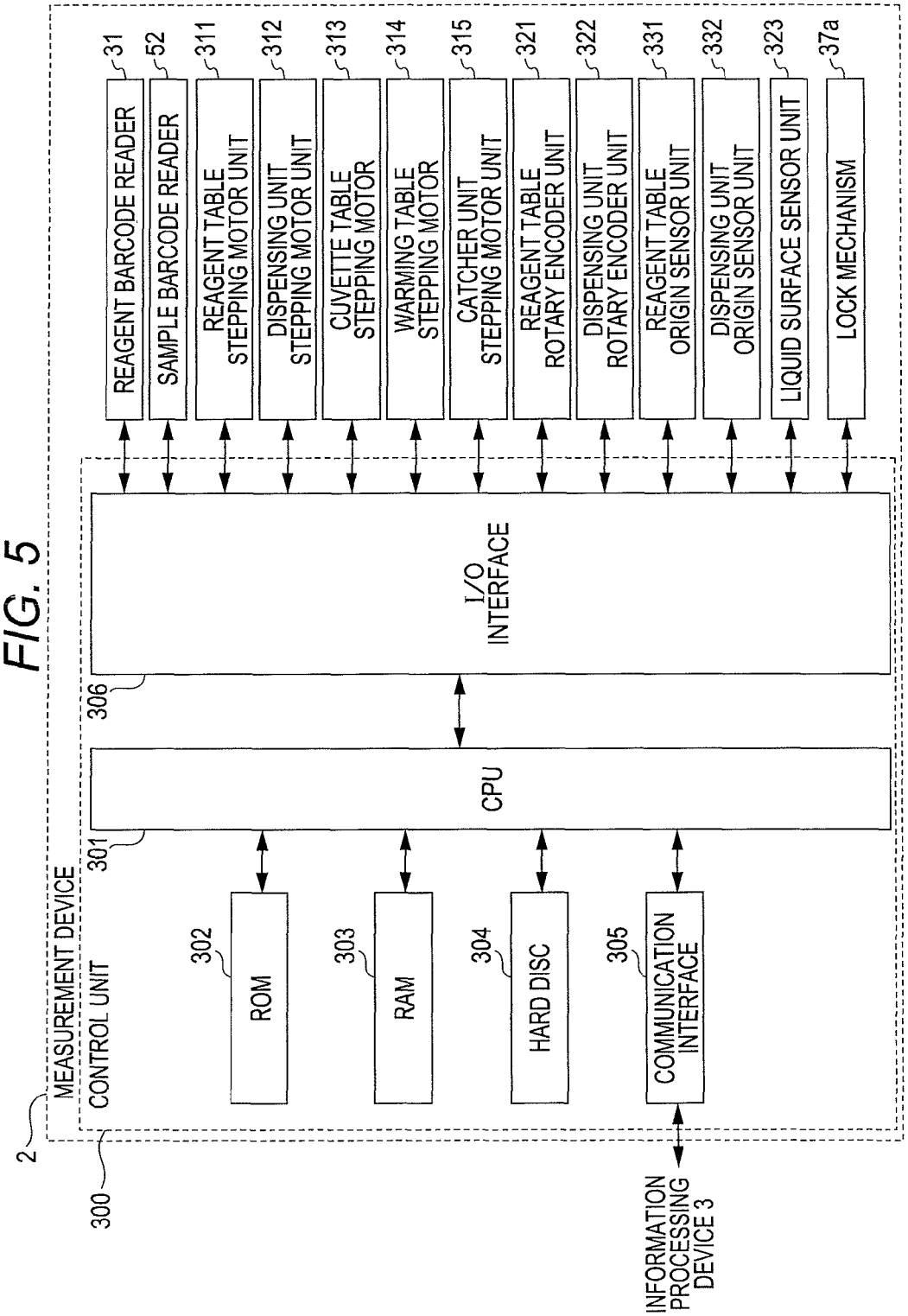
FIG. 5 is a block diagram showing a circuit configuration of a measurement device.

FIG. 5 is a block diagram showing a circuit configuration of the measurement device 2.

The measurement device 2 includes a control unit 300, a reagent barcode reader 31, a sample barcode reader 52, a reagent table stepping motor unit 311, a dispensing unit stepping motor unit 312, a cuvette table stepping motor 313, a warming table stepping motor 314, a catcher unit stepping motor unit 315, a reagent table rotary encoder unit 321, a dispensing unit rotary encoder unit 322, a liquid surface sensor unit 323, a reagent table origin sensor unit 331, a dispensing unit origin sensor unit 332, and a lock mechanism 37a. The control unit 300 includes a CPU 301, a ROM 302, a RAM 303, a hard disc 304, a communication interface 305, and an I/O interface 306.

The CPU 301 executes computer programs stored in the ROM 302 and the computer programs loaded in the RAM 303. The RAM 303 is used to read out the computer programs recorded on the ROM 302 and the hard disc 304. The RAM 303 is also used as a work region of the CPU 301 when executing the computer program. The hard disc 304 is installed with various computer programs to be executed by the CPU 301 such as operating system and application program, as well as data used in executing the computer program. That is, the hard disc 404 is installed with a control program for causing the CPU 301 to control each unit of the measurement device 2. The transmission and reception of data can be carried out with respect to the information processing device 3 by the communication interface 305.

The CPU 301 controls the reagent barcode reader 31, the sample barcode reader 52, the reagent table stepping motor unit 311, the dispensing unit stepping motor unit 312, the reagent table rotary encoder unit 321, the dispensing unit rotary encoder unit 322, the liquid surface sensor unit 323, the reagent table origin sensor unit 331, and the dispensing unit origin sensor unit 332 through the I/O interface.

The reagent table stepping motor unit 311 is configured by a plurality of stepping motors for rotatably driving the first reagent table 11 and the second reagent table 12 independent from each other. The dispensing unit stepping motor unit 312 is configured by a rotation motor 231 and a raising and lowering motor 232 of the first reagent dispensing unit 23, as well as a rotation motor and a raising and lowering motor of the first sample dispensing unit 21, the second sample dispensing unit 22, the second reagent dispensing unit 24, and the third reagent dispensing unit 25. Such rotation motor and raising and lowering motor are stepping motors.

The cuvette table stepping motor 313 is configured by a stepping motor for rotatably driving the cuvette table 15. The warming table stepping motor 314 is configured by a stepping motor for rotatably driving the warming table 16. The catcher unit stepping motor unit 315 is configured by a plurality of stepping motors for rotating the first catcher unit 26 and the second catcher unit 27.

The reagent table rotary encoder unit 321 is configured by a plurality of rotary encoders capable of detecting rotation direction and rotation amount of the plurality of stepping motors included in the reagent table stepping motor unit 311 respectively. The reagent table origin sensor unit 331 is configured by a plurality of origin sensors for detecting that the rotations positions of the plurality of stepping motors included in the reagent table stepping motor unit 311 are origin positions respectively. The CPU 301 receives output signals of the reagent table rotary encoder unit 321 and the reagent table origin sensor unit 331 to recognize how many times the first reagent table 11 and the second reagent table 12 each rotated in the clockwise direction or the counterclockwise direction from the origin position.

The dispensing unit rotary encoder unit 322 is configured by the rotary encoders 235, 236 of the first reagent dispensing unit 23, as well as the rotary encoder of each of the first sample dispensing unit 21, the second sample dispensing unit 22, the second reagent dispensing unit 24, and the third reagent dispensing unit 25. That is, the dispensing unit rotary encoder unit 322 is configured by a plurality of rotary encoders capable of detecting rotation direction and rotation amount of the plurality of stepping motors included in the dispensing unit stepping motor unit 312 respectively. The dispensing unit origin sensor unit 332 is configured by a plurality of origin sensors for detecting that the rotation positions of the plurality of stepping motors included in the dispensing unit stepping motor unit 312 are origin positions respectively. The CPU 301 receives output signals of the dispensing unit rotary encoder unit 322 and the dispensing unit origin sensor unit 332 to recognize how many times the arms 21a, 22a, 23a, 24a, 25a of the first sample dispensing unit 21, the second sample dispensing unit 22, the first reagent dispensing unit 23, the second reagent dispensing unit 24, and the third reagent dispensing unit 25 each rotated in the clockwise direction or the counterclockwise direction from the origin position, and to what extent the arms moved to the upper side or the lower side from the origin position (reference height) in the height direction.

The liquid surface sensor 323 is configured by the capacitance sensor 23d of the first reagent dispensing unit 23, as well as the capacitance sensors of the first sample dispensing unit 21, the second sample dispensing unit 22, the second reagent dispensing unit 24, and the third reagent dispensing unit 25. The CPU 301 receives an output signal of the liquid surface sensor unit 323 to recognize whether or not the pipettes 21c, 22c, 23c, 24c, 25c of the first sample dispensing unit 21, the second sample dispensing unit 22, the first reagent dispensing unit 23, the second reagent dispensing unit 24, and the third reagent dispensing unit 25 contacted the liquid surface.

The lock mechanism 37a is arranged to prohibit the opening of the cover 37 of the measurement device 2. The lock mechanism 37a is configured by a solenoid coil, or the like. The CPU 301 can ON/OFF control the lock mechanism, so that the prohibition/permission of the opening of the cover 37 can be controlled.

Figure 6:
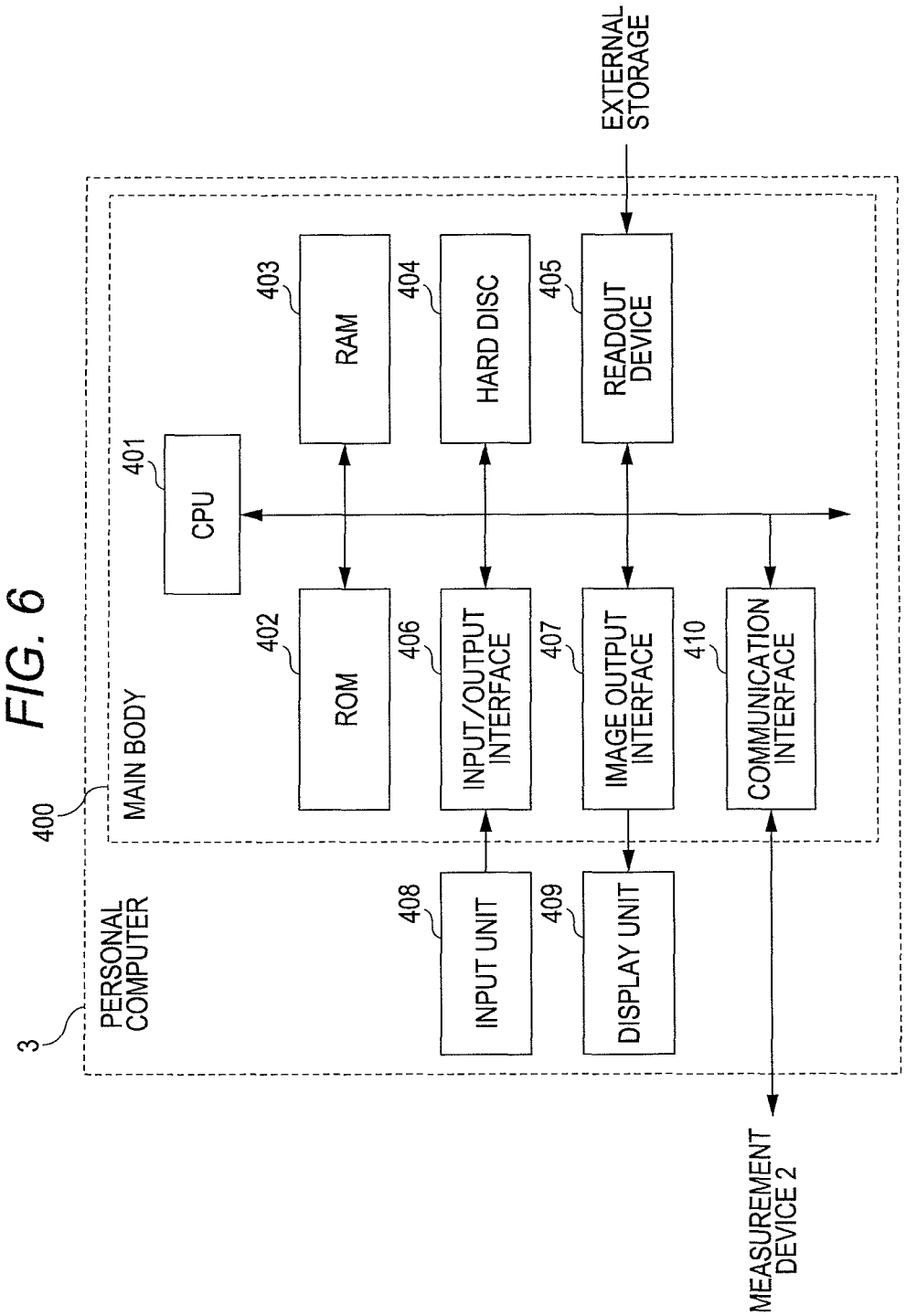
FIG. 6 is a block diagram showing a configuration of the information processing device.

FIG. 6 is a block diagram showing a configuration of the information processing device 3.

The information processing device 3 includes a personal computer, and is configured by a main body 400, an input unit 408, and a display unit 409. The main body 400 includes a CPU 401, a ROM 402, a RAM 403, a hard disc 404, a readout device 405, an input/output interface 406, an image output interface 407, and a communication interface 410.

The CPU 401 executes computer programs stored in the ROM 402 and the computer programs loaded in the RAM 402. The RAM 403 is used to read out the computer programs recorded on the ROM 402 and the hard disc 404. The RAM 403 is also used as a work region of the CPU 401 when executing the computer program.

The hard disc 404 is installed with various computer programs to be executed by the CPU 401 such as operating system and application program, as well as data used in executing the computer program. That is, the hard disc 404 is installed with a computer program for causing the computer to function as the information processing device according to the present embodiment.

The readout device 405 is configured by a CD drive, a DVD drive, or the like, and can read out the computer program and the data recorded in the recording medium. The input unit 408 including mouse and keyboard is connected to the input/output interface 406, so that the user can use the input unit 408 to input data to the information processing device 3. The image output interface 407 is connected to a display unit 409 configured by a CRT, a liquid crystal panel, or the like, and outputs a video signal corresponding to the image data to the display unit 409. The display unit 409 displays images based on the input video signal. The information processing device 3 can transmit and receive data with respect to the measurement device 2 by the communication interface 410.

[Operation of Sample Analyzer]

The operation of the sample analyzer 1 according to the present embodiment will be described below.

<Analyzing Procedure for Every Sample>

First, the procedure for analyzing the sample will be described. The analyzing procedure of the sample differs depending on the measurement item (PT, APTT, etc.) of the sample. The measurement item of the sample is specified by the measurement order. In the sample analyzer 1, the measurement order can be registered by the user, and the measurement order can be accepted from the server device (not shown). That is, when registering the measurement order, the user operates the input unit 408 of the information processing device 3 to input the measurement order to the sample analyzer 1. When accepting the measurement order from the server device, the user registers the measurement order in the server device in advance.

The sample rack 60 accommodating a plurality of sample containers 61 is set in the pre-analysis rack holding region of the transport path 51 by the user. The sample rack 60 is moved to the back side in the pre-analysis rack holding region, and then moved towards the left in the transport region. In this case, the barcode label attached to the sample container 61 is read by the sample barcode reader 52. The sample ID is recorded in the barcode of the sample container 61, and the information processing device 3 acquires the measurement order of the sample with the read sample ID as the key. That is, the measurement order corresponding to the sample ID is read from the hard disc 404 of the information processing device 3 if the measurement order is registered in the sample analyzer 1 by the user, and the sample ID is transmitted from the information processing device 3 to the server device if the measurement order is acquired from the server device so that the server device then transmits the measurement order corresponding to the received sample ID to the information processing device 3 and the information processing device 3 receives the measurement order.

The sample rack 60 is then positioned at a predetermined place in the transport region. After the aspiration of the sample is finished in the transport region, the sample rack 60 is moved towards the left in the transport region and then moved to the front side in the post-analysis rack holding region.

The first sample dispensing unit 21 aspirates the sample of the sample container 61 positioned at a predetermined sample aspirating position 53 of the transport region of the transport path 51. The sample aspirated by the first sample dispensing unit 21 is discharged to a cuvette set in the cuvette holding hole 15*a* positioned at a sample discharging position 18 at the front side position of the cuvette table 15.

The second sample dispensing unit 22 aspirates the sample accommodated in the cuvette at the sample aspirating position 19 or the sample of the sample container 61 positioned at a predetermined sample aspirating position 54 of the transport region of the transport path 51. The sample aspirated by the second sample dispensing unit 22 is discharged to a cuvette set in the cuvette transport unit 32. The second sample dispensing unit 22 can aspirate the diluted solution set in the diluted solution transport unit 33. In this case, the sample dispensing unit 22 aspirates the diluted solution at the diluted solution aspirating position 37 before aspirating the sample, and then aspirates the sample at the sample aspirating position 19 or 54.

When the measurement order including a plurality of measurement items is acquired for one sample, the sample is divided into cuvettes for the number of measurement items from the cuvette set in the cuvette holding hole 15*a* of the cuvette table 15. Each cuvette corresponds to the measurement item one by one, and the sample divided into the cuvette is measured for the measurement item corresponding to the relevant cuvette.

The cuvette transport unit 32 is driven towards the right on the rail at a predetermined timing when the sample is discharged (divided) to the accommodated cuvette. The cuvette accommodating the sample set in the cuvette transport unit 32 is then gripped by the first catcher unit 26, and set in the cuvette holding hole 16*a* of the warming table 16. The sample accommodated in the cuvette is warmed for a time corresponding to the measurement item in the warming table 16. For instance, the sample is warmed for three minutes if the measurement item is PT, and the sample is warmed for one minute if the measurement item is APTT.

After the sample is warmed, the reagent is mixed to the sample. Whether the sample mixed with the reagent is measured by the detection unit 40 or again warmed differs depending on the measurement item. For instance, if the measurement item is the PT, the PT reagent is dispensed to the cuvette accommodating the warmed sample, and thereafter, optically measured in the detection unit 40.

In this case, the cuvette held in the cuvette holding hole 16*a* of the warming table 16 is gripped by the third catcher unit 28, and positioned at the reagent discharging position 39*a* or 39*b*. The reagent in the predetermined reagent container 200 arranged in the first reagent table 11 or the second reagent table 12 is aspirated by the second reagent dispensing unit 24 or the third reagent dispensing unit 25, and the reagent is discharged at the reagent discharging position 39*a* or 39*b*. After the reagent is discharged in such manner, the third catcher unit 28 sets the cuvette to which the reagent is discharged in the holding hole 41 of the detection unit 40. Thereafter, the optical information is detected from the measurement specimen accommodated in the cuvette in the detection unit 40.

A case in which the reagent is mixed to the warmed sample and again warmed will now be described. For instance, if the measurement item is the APTT, the APTT reagent is dispensed to the cuvette accommodating the warmed sample, and thereafter, warmed again for two minutes in the warming table 16. Thereafter, calcium chloride solution is dispensed into the cuvette, and optical measurement is carried out in the detection unit 40. In the case of the measurement item for warming the sample twice, the sample is warmed for a predetermined time in the warming table 16, and then the second catcher unit 27 grips the cuvette accommodating the sample set in the holding hole 16*a*, and moves the same to the reagent discharge position 38. The first reagent dispensing unit 23 aspirates the reagent of the predetermined reagent container 200 arranged in the first reagent table 11 or the second reagent table 12, and discharges the reagent at the reagent discharging position 38. After the reagent is discharged, the second catcher unit 27 stirs the relevant cuvette and again sets the same in the cuvette holding hole 16*a* of the warming table.

The cuvette held in the cuvette holding hole 16*a* of the warming table 16 is gripped by the third catcher unit 28 and positioned at the reagent discharging position 39*a* or 39*b*. The second reagent dispensing unit 24 or the third reagent dispensing unit 25 aspirates the reagent of the predetermined reagent container 200 arranged in the first reagent table 11 or the second reagent table 12, and discharges the reagent at the reagent discharging position 39*a* or 39*b*. After the reagent is discharged in such manner, the third catcher unit 28 sets the cuvette to which the reagent is discharged in the holding hole 41 of the detection unit 40. Thereafter, the optical information is detected from the measurement specimen accommodated in the cuvette in the detection unit 40.

The optical information detected by the detection unit 40 is transmitted to the information processing device 3. The CPU 401 of the information processing device 3 processes the acquired optical information and obtains the analysis result of the sample. The analysis result obtained in such manner is corresponded with the sample information such as the sample ID and stored in the hard disc 404, and output to the display unit 409.

The cuvette, of which detection by the detection unit 40 is terminated and which is no longer necessary, is moved to immediately above the discarding port 35 while being gripped by the third catcher unit 28, and then discarded to the discarding port 35. When the cuvette held in the cuvette holding hole 15*a* of the cuvette table 15 is also terminated with the analysis and is no longer necessary, the cuvette table 15 is rotated and positioned to the location close to the second catcher unit 27. The second catcher unit 27 grips the cuvette that is no longer necessary and held in the cuvette holding hole 15*a*, and discards the same in the discarding port 36.

<Registering Operation of Reagent Information>

After the sample analyzer 1 is shut down, the reagent set in the first reagent table and the second reagent table is moved to a refrigerator or the like and may be saved until the sample analyzer 1 is used the next time. Furthermore, the reagent taken out from the sample analyzer 1 may be replaced with a new reagent or the reagent may be added to the reagent container. Therefore, in the initialization operation executed immediately after the sample analyzer 1 is started up, the reagent information related to the reagent set in the first reagent table and the second reagent table is registered. The registering operation of the relevant reagent information will be described below.

Figure 7:
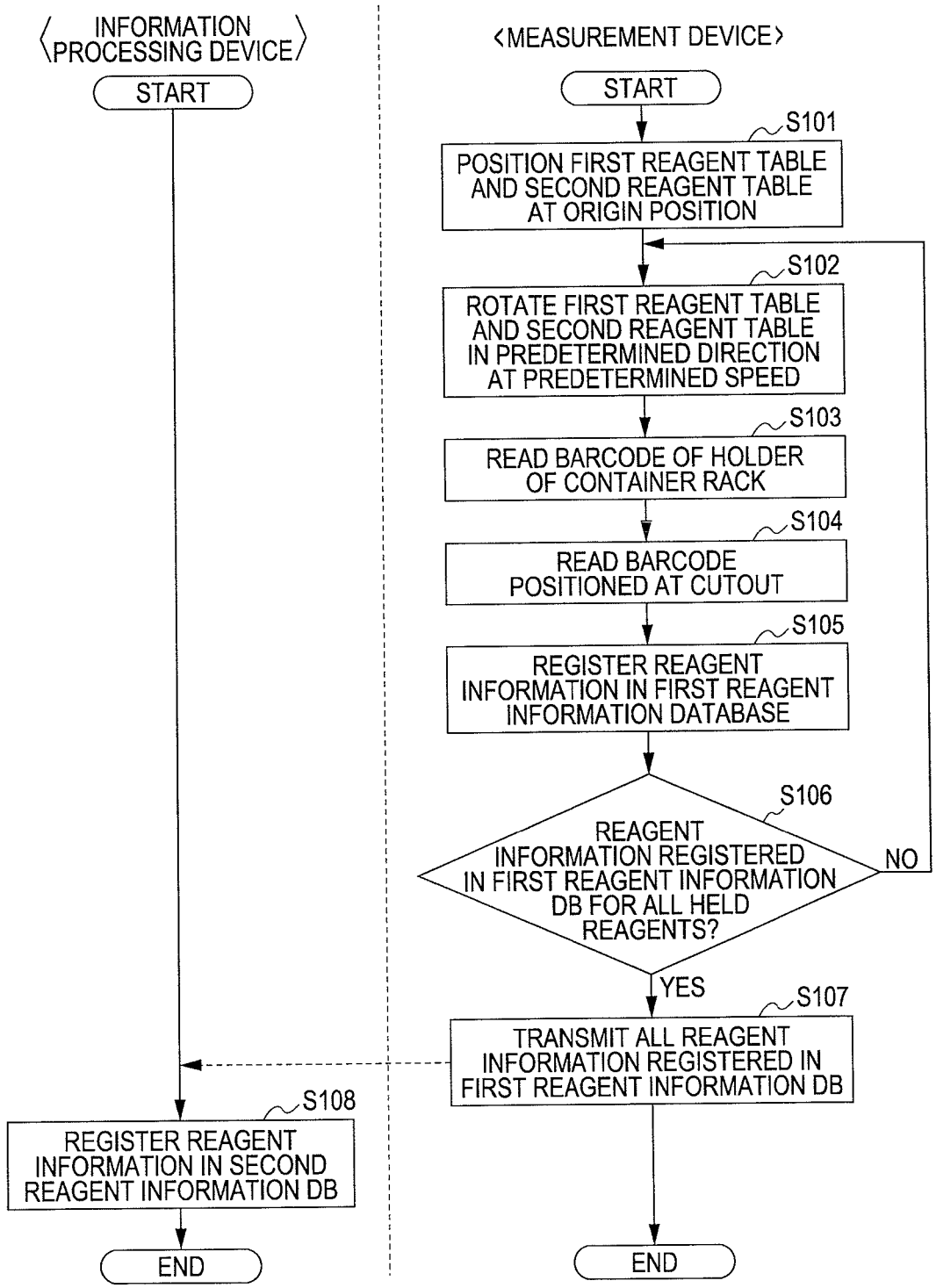
FIG. 7 is a flowchart showing the flow of the registering operation of the reagent information.

FIG. 7 is a flowchart showing the flow of the registering operation of the reagent information. In the registering operation of the reagent information, the CPU 301 of the measurement device 2 controls the reagent table stepping motor unit 311 to rotatably drive the first reagent table 11 and the second reagent table 12 and position them respectively at the origin position (step S101). Thereafter, the CPU 301 controls the reagent table stepping motor unit 311 to rotate the first reagent table 11 and the second reagent table 12 in a predetermined direction at a predetermined speed (step S102), and causes the barcode reader 31 to read the barcode label attached to the outer peripheral surface of the holder of the container rack (step S103). Therefore, in which holder of which container rack the relevant holder is arranged can be recognized.

Thereafter, the CPU 301 controls the reagent table stepping motor unit 311 to rotatably drive the first reagent table 11 and the second reagent table 12 and causes the barcode reader 31 to read the barcode positioned at the cutout of the relevant holder (step S104). In this case, the barcode label attached to the reagent container 200 is read if the reagent container 200 is accommodated, and the barcode label attached to the inner peripheral surface of the holder is read if the reagent container 200 is not accommodated. Whether or not the reagent container 200 is held in the holder can be recognized in such manner. Furthermore, if the reagent container 200 is held in the holder, the type of reagent accommodated in the reagent container 200 is identified by the barcode information read from the barcode label 200a. The CPU 301 stores the information specifying the container rack, the information specifying the holder, the information on the type of reagent held in the holder (if reagent container is not held, information indicating the same), or the like obtained in the above manner in the first reagent information database 500 arranged in the hard disc 304 (step S105). FIG. 8A is a schematic view showing a configuration of the first reagent information database 500. The first reagent information database 500 includes a field 501 for storing the container rack ID or the information specifying the container rack, a field 502 for storing the holder number or the information specifying the holder of the container rack, a field 503 for storing the information on the type of reagent, or the like. The first reagent information database 500 also includes a field 504 for storing the information on the liquid level of the reagent to be described later. At this time point, no information is stored in the field 504 since the liquid level of the reagent is not detected even once.

The CPU 301 determines whether or not the information is stored in the first reagent information database 500 for all holders of all container racks set in the first reagent table 11 and the second reagent table 12 (step S106), where if the holder in which the storage of information is not carried out exists (NO in step S106), the process returns to step S102, and the first reagent table 11 and the second reagent table 12 are rotated to the position where the barcode label of the next holder faces the barcode reader 31.

If the information is stored in the first reagent information database 500 for all the holders of all the container racks set in the first reagent table 11 and the second reagent table 12 in step S106 (YES in step S106), the CPU 301 transmits all information stored in the first reagent information database 500 to the information processing device 3 (step S107), and terminates the process.

When the information processing device 3 receives the reagent information, the CPU 401 of the information processing device 3 stores the reagent information in the second reagent information database 600 arranged in the hard disc 404 based on the received information (step S108), and terminates the process. FIG. 8B is a schematic view showing a configuration of the second reagent information database 600. The second reagent information database 600 includes a field 601 for storing the container rack ID, a field 602 for storing the holder number, a field 603 for storing the information on the type of reagent, or the like, similar to the first reagent information database 500. The second reagent information database 600 also includes a field 604 for storing a liquid level storage flag indicating whether or not the liquid level information is stored in the first reagent information database 500. In the reagent information transmitted from the measurement device 2, the liquid level storage flag is set to "1" in the second reagent information database 600 for the reagents containing the liquid level information, and the liquid level storage flag is set to "0" in the second reagent information database 600 for reagents not containing the liquid level information.

<Reagent Replacement Operation>

Figure 9A:
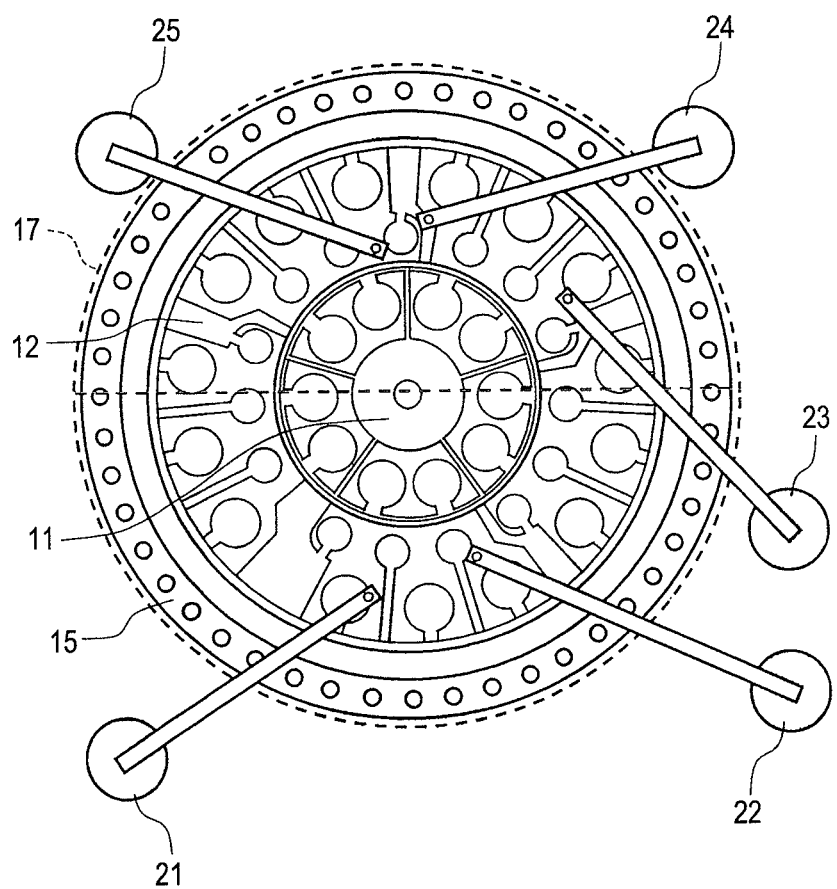
FIG. 9A is a plan view showing a state of a table cover in which replacement or addition of the reagent is not carried out.
Figure 9B:
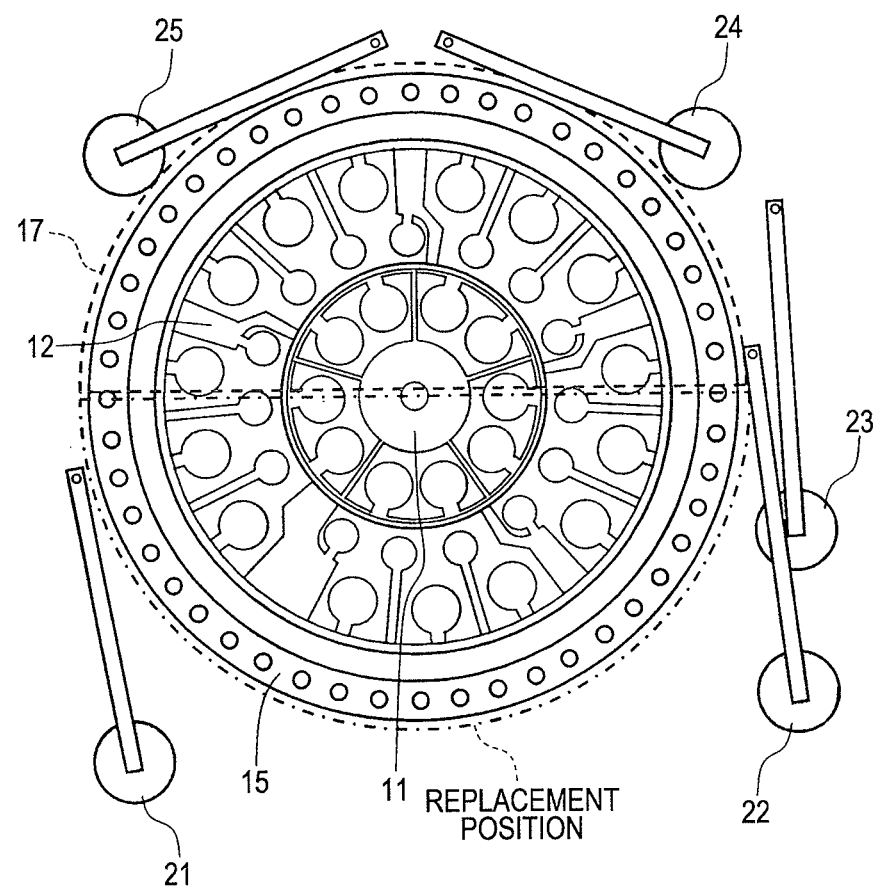
FIG. 9B is a plan view showing a state of the table cover in which replacement or addition of the reagent is carried out.

The reagent replacement operation of the sample analyzer 1 will now be described. FIG. 9A is a plan view showing a state of the normal table cover 17 in which replacement or addition of the reagent is not carried out, and FIG. 9B is a plan view showing a state of the table cover 17 in which replacement or addition of the reagent is carried out.

In the measurement device 2 in a state (standby state) waiting for the power supply to be turned ON and the sample to be measured or in a state of executing the measurement of the sample, the cover 37 is closed and the cover 37 is locked by the lock mechanism 37a, as shown in FIG. 1. In such state, the table cover 17 covers the upper surface of the first reagent table 11 and the second reagent table 12 (hereinafter referred to as "reagent table group") as well as the cuvette table 15, as shown in FIG. 9A. In this case, the first sample dispensing unit 21, the second sample dispensing unit 22, the first reagent dispensing unit 23, the second reagent dispensing unit 24, and the third reagent dispensing unit 25 (hereinafter referred to as "dispensing unit group") carry out dispensing of the sample or the reagent through a plurality of holes formed in the table cover 17.

When replacing or adding the reagent, the user operates the input unit 408 of the information processing device 3 to input the instruction to start the replacement or the addition of the reagent to the information processing device 3. The CPU 401 of the information processing device 3 instructs the measurement device 2 to unlock the cover 37 when receiving the input. The CPU 301 of the measurement device 2 controls the lock mechanism 37a to unlock the cover 37, and controls the dispensing unit group to evacuate to a position not in the region covered by the table cover 17 shown in FIG. 9A (hereinafter referred to as "evacuating position") so that the user can open the cover 37.

The user then opens the cover 37 and folds the table cover 17 at the central part. Only the reagent table group and the upper half region of the cuvette table 15 are then covered by the table cover 17 (portion of dotted line indicates the region covered by the table cover 17, and portion of chain dashed line indicates the region not covered by the table cover 17), as shown in FIG. 9B. In this case, the region not covered by the table cover 17 (hereinafter referred to as "replacement position") is formed, and hence the user can replace or add the reagent through such replacement position. In other words, the user takes out the first container rack 13 and the second container rack 14 through the replacement position, replaces or adds the reagent, and then again sets the container rack in the reagent table. Alternatively, the user replaces or adds the reagent directly to the reagent container 200 arranged in the container rack.

After the reagent is replaced or added, the user closes the table cover 17 and also closes the cover 37. After the cover 37 is closed, the CPU 301 controls the lock mechanism 37a to again lock the cover 37.

Subsequently, the reagent information is registered to the reagent information table with respect to the reagent container positioned at the replacement position of the first reagent table 11 and the second reagent table 12. This operation is similar to the registering operation of the reagent information described above other than that all reagent containers of the first reagent table 11 and the second reagent table 12 are not the target, and the reagent container positioned at the replacement position of the first reagent table 11 and the second reagent table 12 is the target, and hence the description will be omitted.

<Sample Analyzing Operation>

In the sample analyzer 1 according to the present embodiment, each of the first sample dispensing unit 21, the second sample dispensing unit 22, the first reagent dispensing unit 23, the second reagent dispensing unit 24, and the third reagent dispensing unit 25 rotatably moves the pipette 21c, 22c, 23c, 24c, 25c to immediately above the cuvette or the reagent container 200 when dispensing the sample or the reagent, and then lowers the pipette 21c, 22c, 23c, 24c, 25c first by the first speed and then lowers the pipette 21c, 22c, 23c, 24c, 25c by the second speed slower than the first speed from the middle to enter the distal end of the pipette 21c, 22c, 23c, 24c, 25c into the sample or the reagent. The pipette 21c, 22c, 23c, 24c, 25c can be lowered at high speed by carrying out the speed control of two stages, and furthermore, the liquid surface can be accurately detected by lowering at low speed when the pipette distal end is in contact with the liquid surface, so that the pipette is prevented from entering the liquid deeply.

More specifically describing, in the first sample dispensing unit 21 and the second sample dispensing unit 22, the pipette is lowered at high speed by the first speed until the fixedly set speed switching height, and then the pipette is lowered at low speed by the second speed on the lower side of the speed switching height.

In the first reagent dispensing unit 23, the second reagent dispensing unit 24, and the third reagent dispensing unit 25, the pipette is lowered at high speed by the first speed up to the variable speed switching height set according to the level of the reagent liquid surface, and then the pipette is lowered at low speed by the second speed on the lower side of the speed switching height. That is, the CPU 301 detects the position (hereinafter referred to as "liquid level") in the up and down direction of the pipette when the liquid surface of the reagent is detected by the liquid surface sensor unit 323, sets the position on the upper side of the liquid level by a predetermined distance as the speed switching height, and executes the operation described above when dispensing the reagent. Therefore, the distance of lowering the pipette at the first speed can be made as large as possible, so that the dispensing operation can be carried out at as high speed as possible.

The liquid level of the reagent can be obtained by subtracting the height corresponding to the aspiration amount of the reagent from the liquid level of when the liquid surface is detected in the previous reagent dispensing operation. Thus, the high speed reagent dispensing operation can be continuously carried out next and subsequent times after the reagent dispensing is carried out once. However, after the sample analyzer 1 is shut down, the reagent set in the first reagent table and the second reagent table is moved to the refrigerator, or the like and may be stored therein until the sample analyzer 1 is used the next time. Furthermore, the reagent taken out from the sample analyzer 1 may be replaced with a new reagent or the reagent may be added to the reagent container. Therefore, the amount of reagent in each reagent container may not be the same as the amount of reagent of when the sample analyzer is shut down the previous time immediately after the sample analyzer 1 is started up. Even if the sample analyzer 1 is operating, the reagent at the replacement position that may be replaced or added by the user with the table cover 17 opened of the reagents set in the first reagent table and the second reagent table may be subjected to replacement or addition of reagent after the replacement or the addition of the reagent is carried out, and thus the amount thereof may not be the same as the amount of reagent of before the reagent replacement operation. That is, the liquid level of the reagent is unknown in the reagent container accommodating the relevant reagent. Therefore, immediately after the start up, the sample analyzer 1 first executes the operation (hereinafter referred to as "initial liquid level detection operation") for detecting the liquid level of the reagent for the reagent corresponding to the measurement item included in the accepted measurement order of all the reagents set in the first reagent table and the second reagent table, and acquires the liquid level of the reagent. Furthermore, the sample analyzer 1 sets the speed switching height based on the liquid level detected in such manner, and thereafter, lowers the pipette in the above manner using the set speed switching height to aspirate the reagent. Immediately after the reagent replacement operation is terminated, the sample analyzer 1 first executes the initial liquid level detection operation for the reagent corresponding to the measurement item included in the received measurement order of all the reagents at the replacement position of the table cover 17 during the execution of the reagent replacement operation, sets the speed switching height based on the detected liquid level, and thereafter, lowers the pipette as described above using the set speed switching height to aspirate the reagent.

Figure 10A:
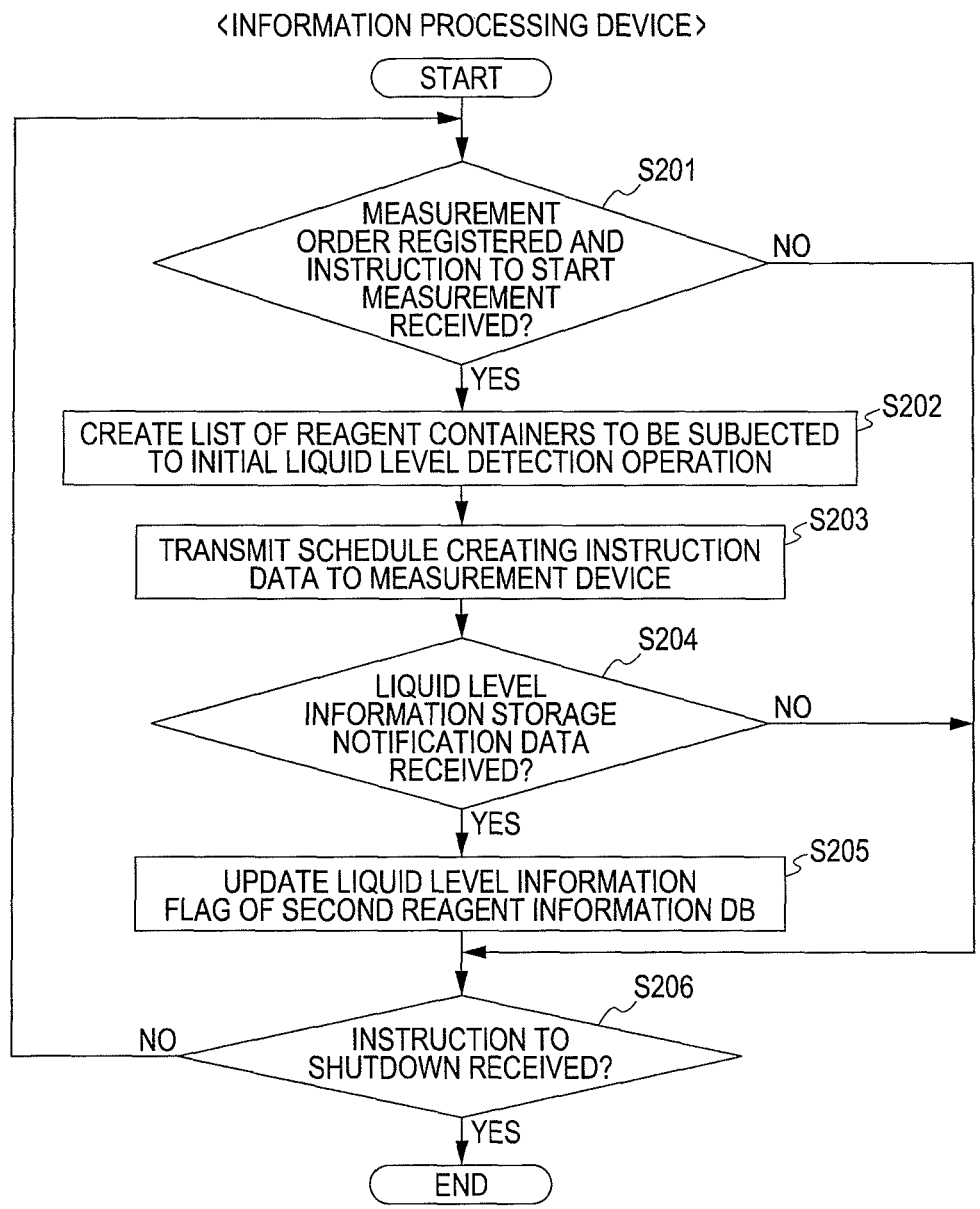
FIG. 10A is a flowchart showing the processing procedure of the CPU of the information processing device in the sample analyzing operation.
Figure 10C:
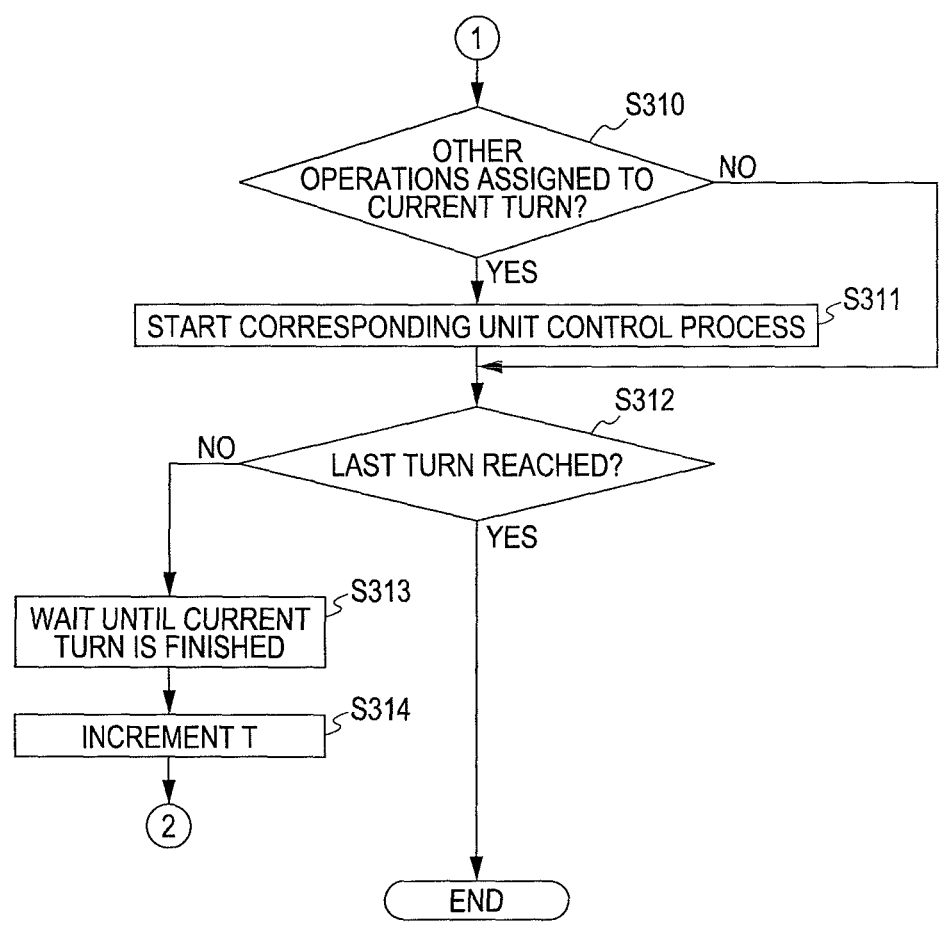
FIG. 10C is a flowchart (second half) showing the processing procedure of the CPU of the measurement device in the sample analyzing operation.

The sample analyzing operation will be specifically described below. FIG. 10A is a flowchart showing the processing procedure of the CPU 401 of the information processing device 3 in the sample analyzing operation, and FIGS. 10B and 10C are flowcharts showing the processing procedure of the CPU 301 of the measurement device 2 in the sample analyzing operation.

First, the CPU 401 of the information processing device 3 determines whether or not the measurement order is registered and the instruction to start the measurement is received (step S201). The criterion in this process is whether or not the measurement order input from the user is registered and the instruction to start the measurement is received from the user through the input unit 408 when the user directly inputs the measurement order to the sample analyzer 1, and whether or not the sample rack 60 is transported by the transport unit 50, the sample ID read by the sample barcode 52 from the sample container 61 accommodated in the sample rack 60 is transmitted from the information processing device 3 to the server device, and the information processing device 3 received the measurement order corresponding to the sample ID from the server device when receiving the measurement order from the server.

If the criterion in step S201 is not satisfied (NO in step S201), the CPU 401 proceeds the process to step S206. If the criterion in step S201 is satisfied (YES in step S201), the CPU 401 creates a list of reagent containers to become the target of the initial liquid level detection operation (step S202). In this process, a list of holding positions of the reagent containers accommodating the reagent corresponding to the measurement item included in the received measurement order is created, the reagent container accommodating the reagent in which "0" is set for the liquid level information storage flag in the second reagent information database 600, that is, the reagent in which the liquid level information is not stored in the first reagent information database 500. That is, if the sample analysis is carried out for the first time after the sample analyzer 1 is started, the reagent container accommodating the reagent corresponding to the measurement item included in the received measurement order of all the reagents set in the first reagent table and the second reagent table will be contained in the list. If the sample analysis is carried out after the termination of the reagent replacement operation, the reagent container accommodating the reagent corresponding to the measurement item included in the received measurement order of all the reagents at the replacement position of the table cover 17 during the execution of the reagent replacement operation will be contained in the list. The list contains information on the holding position at where the reagent container to be subjected to the initial liquid level detection operation is held.

The CPU 401 transmits the schedule creating instruction data to the measurement device 2 (step S203). The hard disc 404 stores information on the protocol (amount of sample, warming time of sample, type of reagent, amount, etc.) of the sample measurement for every measurement item. The CPU 401 reads out the information on the protocol corresponding to the measurement item included in the received measurement order from the hard disc 404, and generates the schedule creating instruction data while corresponding the sample ID and the measurement protocol information. The schedule creating instruction data also includes a list of reagent containers created in step S202.

The CPU 401 determines whether or not the liquid level information storage notification data to be described later is received from the measurement device 2 (step S204), and changes the liquid level information storage flag corresponding to the reagent which liquid level information is stored in the first reagent information database 500 to "1" (step S205) in the second reagent information database 600 based on the liquid level information storage notification data if the liquid level information storage notification data is received (YES in step S204). The CPU 401 thereafter proceeds the process to step S206. If the liquid level information storage notification data is not received in step S204 (NO in step S204), the CPU 401 proceeds the process to step S206.

In step S206, the CPU 401 determines whether or not the instruction to shutdown is received from the user (step S206), and returns the process to step S201 if the instruction to shutdown is not received (NO in step S206). If the instruction to shutdown is received (YES in step S206), the CPU 401 terminates the process.

The processes of the CPU 301 of the measurement device 2 will now be described with reference to FIG. 10B and FIG. 10C. The CPU 301 of the measurement device 2 waits for the reception of the schedule creating instruction data (NO in step S301), and the CPU 301 creates the schedule of the sample measurement (step S302) when the measurement device 2 receives the schedule creating instruction data (YES in step S301).

Figure 11:
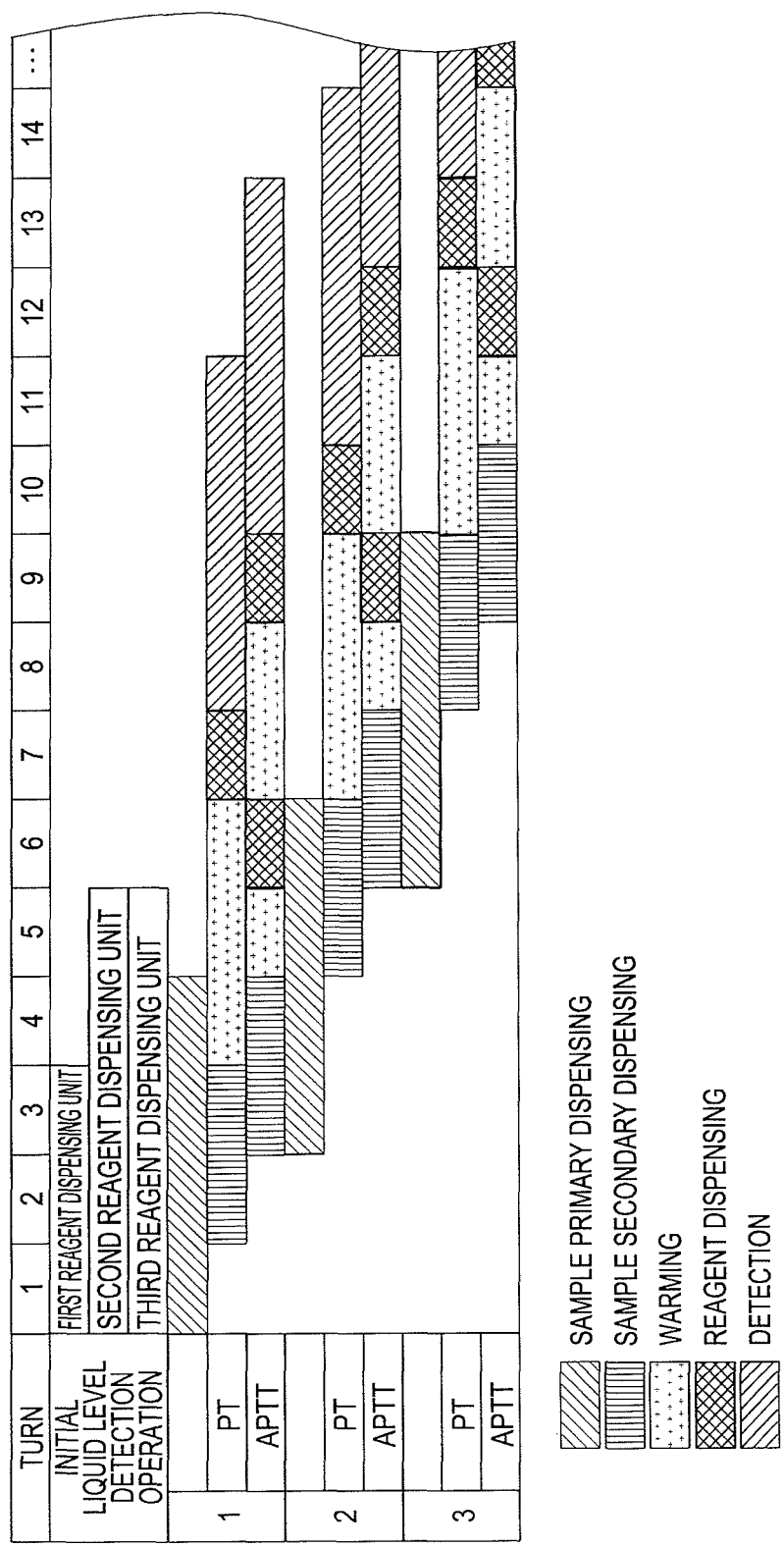
FIG. 11 is a timing chart partially showing one example of the schedule for sample measurement.

FIG. 11 is a timing chart partially showing one example of the schedule for sample measurement. As shown in the figure, the schedule for sample measurement is created by assigning the operation to be executed for every continuous turn divided by a predetermined time interval (e.g. nine seconds). The CPU 301 assigns the initial liquid level detection operation in the first few turns of the schedule based on the list of reagent containers to be subjected to the initial liquid level detection operation included in the schedule creating instruction data. In the example of FIG. 11, the first reagent dispensing unit 23 is scheduled to execute the initial liquid level detection operation in the first to third turns, and the second reagent dispensing unit 24 and the third reagent dispensing unit 25 are respectively scheduled to execute the initial liquid level detection operation in the first to fifth turns.

In this example, the measurement of the measurement items PT and APTT is instructed for each sample of sample number 1 to 3. For the sample of sample number 1, the primary dispensing (dispensing of the sample from the sample container 61 to the cuvette held in the cuvette table 15 by the first sample dispensing unit 21) of the sample is scheduled in the first to fourth turns, the secondary dispensing (dispensing of the sample from the cuvette held in the cuvette table 15 to the cuvette set in the cuvette transport unit 32 by the second sample dispensing unit 22) of the sample for the PT is scheduled in the second to third turns, and the secondary dispensing of the sample for the APTT is scheduled in the third to fourth turns. For the sample for PT, the warming of the sample is scheduled in the fourth to sixth turns, the dispensing of the PT reagent to the sample is scheduled in the seventh turn, and the optical measurement is scheduled in the eighth to eleventh turns. For the sample for APTT, the warming of the sample is scheduled in the fifth turn, the dispensing of the APTT reagent to the sample is scheduled in the sixth turn, the second warming of the sample is scheduled in the seventh and eighth turns, the dispensing of calcium chloride solution to the sample is scheduled in the ninth turn, and the optical measurement is scheduled in the tenth to thirteenth turns. The schedule similar to the sample number 1 is scheduled to start a few turns afterwards for the sample of sample number 2, and the schedule similar to the sample number 1 is scheduled to start another few turns afterwards for the sample of sample number 3.

Therefore, a plurality of operations is executed simultaneously in parallel in the measurement device 2. For instance, the liquid level detection operation by the first reagent dispensing unit 23, the liquid level detection operation by the second reagent dispensing unit 24, the liquid level detection operation by the third reagent dispensing unit 25, the primary dispensing operation for the sample of sample number 1, and the like are executed in parallel. The CPU 301 creates the schedule so that the same mechanism portion (e.g., first reagent dispensing unit 23) is not used in two operations in the same turn and so that the entire measurement operation of the sample is terminated in as few numbers of turns as possible.

The liquid level detection operation is assigned to the turn before the turn to which the dispensing operation of the reagent is assigned first. In the example of FIG. 11 as well, the liquid surface detection operation is terminated in the fifth turn, and is scheduled in the turn before the dispensing operation (sixth turn) of the APTT reagent of the sample number 1 or the first reagent dispensing operation. Thus, the speed switching height based on the liquid level information can be set from the first reagent dispensing, and the efficiency of the reagent dispensing operation can be realized. If the initial liquid level detection operation is not completed before the first reagent dispensing operation, the schedule is created such that the first reagent dispensing operation is shifted to after the initial liquid level detection operation.

The sample measurement schedule created in the above manner is stored in the hard disc 304.

After creating the sample measurement schedule, the CPU 301 starts the measurement of the sample. First, the CPU 301 sets 1 to the variable T indicating the current turn (step S303). The CPU 301 then references the created schedule and determines whether or not the current turn is the turn assigned with the initial liquid level detection operation (step S304). If the current turn is the turn assigned with the initial liquid level detection operation (YES in step S304), the CPU 301 starts the initial liquid level detection control process (step S305), and proceeds the process to step S306. If the current turn is not the turn assigned with the initial liquid level detection operation (NO in step S304), the CPU 301 proceeds the process to step S306.

In step S306, the CPU 301 references the created schedule and determines whether or not the current turn is the turn assigned with the sample dispensing operation (primary dispensing or secondary dispensing of sample) (step S306). If the current turn is the turn assigned with the sample dispensing operation (YES in step S306), the CPU 301 starts the sample dispensing control process (step S307) and proceeds the process to step S308. If the current turn is not the turn assigned with the sample dispensing operation (NO in step S306), the CPU 301 proceeds the process to step S308.

In step S308, the CPU 301 references the created schedule and determines whether or not the current turn is the turn assigned with the reagent dispensing operation (step S308). If the current turn is the turn assigned with the reagent dispensing operation (YES in step S308), the CPU 301 starts the reagent dispensing control process (step S309) and proceeds the process to step S310. If the current turn is not the turn assigned with the reagent dispensing operation (NO in step S308), the CPU 301 proceeds the process to step S310.

In step S310, the CPU 301 references the created schedule and determines whether or not the current turn is the turn assigned with the operation (other operation) other than the initial liquid surface detection operation, the sample dispensing operation, and the reagent dispensing operation (step S310). If the current turn is the turn assigned with the other operation (YES in step S310), the CPU 301 starts the unit control process for realizing the other operation (step S311) and proceeds the process to step S312. If the current turn is not the turn assigned with the other operation (NO in step S310), the CPU 301 proceeds the process to step S312.

The initial liquid level detection control process can be executed in parallel to the sample dispensing control process and the unit control process. Since the initial liquid level detection operation and the reagent dispensing operation are not assigned to the same turn, the initial liquid level detection control process will not be executed in parallel to the reagent dispensing control process.

In step S312, the CPU 301 determines whether or not the last turn of the created schedule is reached (step S312). If the last turn is not reached (NO in step S312), the CPU 301 waits until the current turn is terminated (i.e., until nine seconds have elapsed from the start of the turn) (step S313), increments the value of the variable indicating the current turn by 1 (step S314), and returns the process to step S304. If the last turn is reached in step S312 (YES in step S312), the CPU 301 terminates the process.

Figure 12:
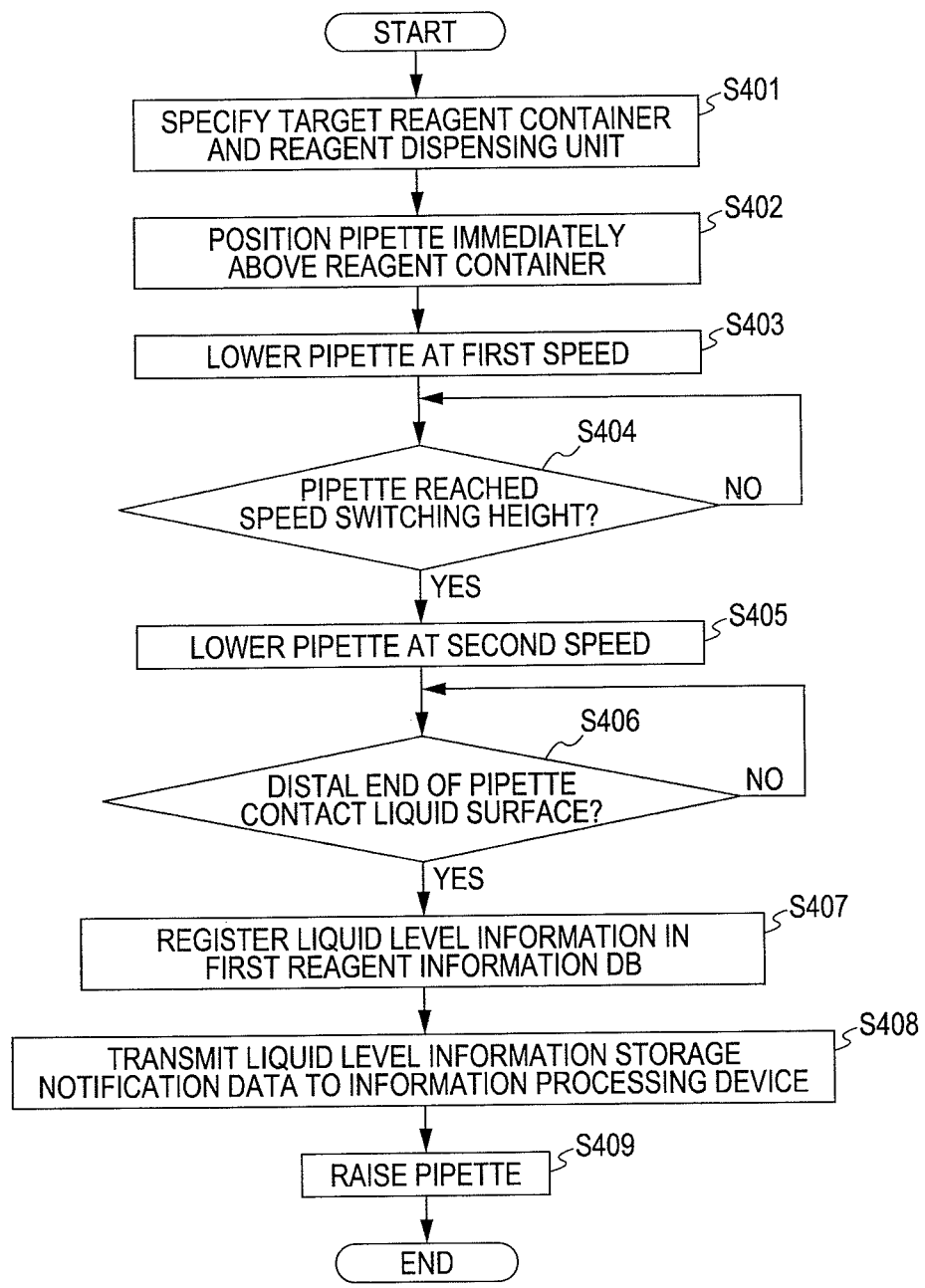
FIG. 12 is a flowchart showing the procedure of the initial liquid level detection control process.

The details of the initial liquid level detection control process will now be described. FIG. 12 is a flowchart showing the procedure of the initial liquid level detection control process. First, the CPU 301 references the sample measurement schedule, and specifies the reagent container to be executed with the initial liquid level detection operation in the current turn, and the reagent dispensing unit for executing the initial liquid level detection operation with respect to the relevant reagent container (step S401). The CPU 301 then controls the reagent table stepping motor unit 311 and the dispensing unit stepping motor unit 312 to position the pipette of the specified reagent dispensing unit immediately above the target reagent container (step S402).

The CPU 301 then controls the dispensing unit stepping motor unit 312 and lowers the pipette of the specified reagent dispensing unit at the first speed (step S403). The CPU 301 monitors the output signal from the dispensing unit rotary encoder unit 322, and determines whether or not the pipette reached the fixed speed switching height stored in the hard disc 304 (step S404). If the pipette has not reached the speed switching height (NO in step S404), the CPU 301 repeats the process of step S404 until the pipette reaches the speed switching height. The fixed speed switching height stored in the hard disc 304 in step S404 is set so as to be a sufficiently distant position even from the highest liquid surface of the reagent accommodated in the reagent container.

If the pipette reached the speed switching height (YES in step S404), the CPU 301 controls the dispensing unit stepping motor unit 312, and lowers the pipette of the specified reagent dispensing unit at the second speed slower than the first speed (step S405). The CPU 301 further monitors the output signal from the liquid surface sensor unit 323, and determines whether or not the distal end of the pipette is contacting the liquid surface (step S406). If the distal end of the pipette is not contacting the liquid surface (NO in step S406), the CPU 301 repeats the process of step S406 until the distal end of the pipette contacts the liquid surface.

If the distal end of the pipette is contacting the liquid surface (YES in step S406), the CPU 301 stores the count value (value reflecting the liquid level at the time point) of the rotary encoder corresponding to the pipette of when the distal end of the pipette contacts the liquid surface in the record corresponding to the reagent container of the first reagent information database 500 as the liquid level information by the output signal from the dispensing unit rotary encoder unit 322 (step S407). Thereafter, the CPU 301 transmits the liquid level information storage notification data indicating that the liquid level information is stored for the relevant reagent to the information processing device 3 (step S408). Furthermore, the CPU 301 controls the dispensing unit stepping motor unit 312 to raise the pipette of the specified reagent dispensing unit (step S409) and terminates the process.

Figure 13:
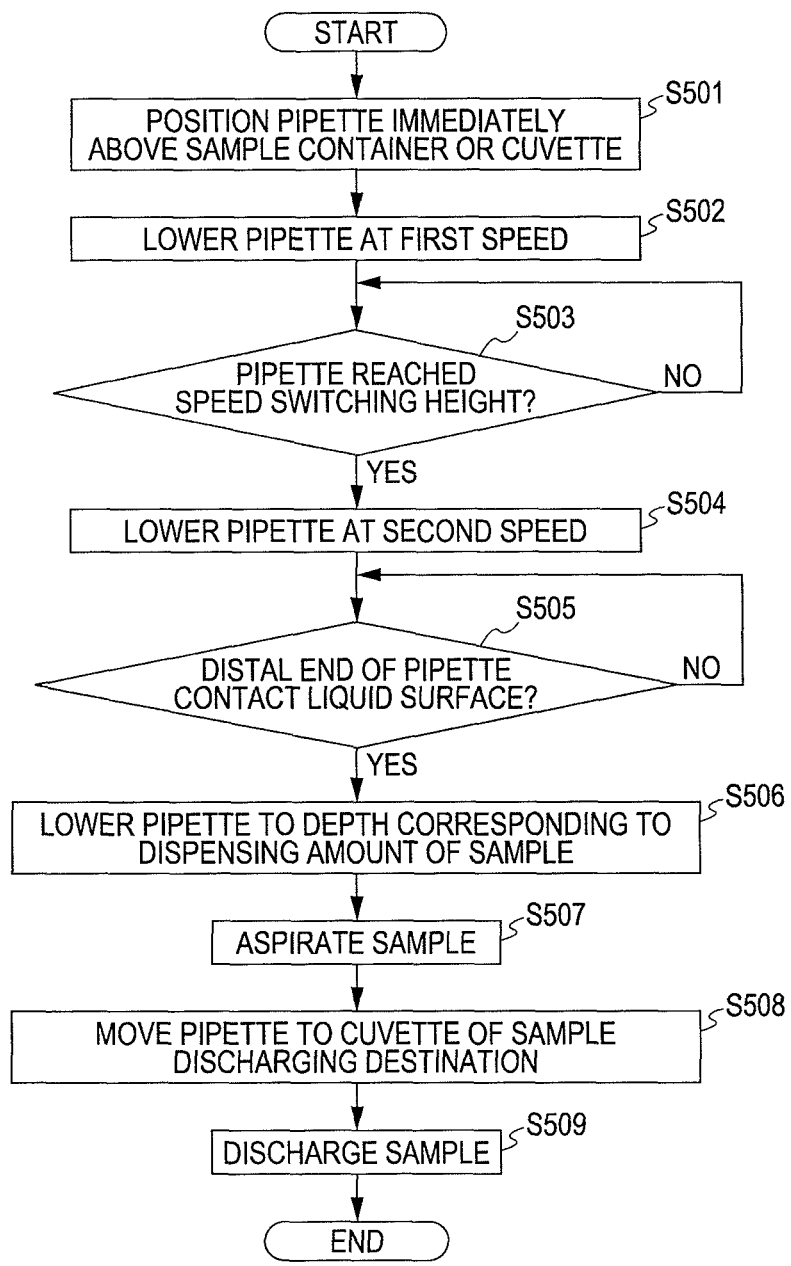
FIG. 13 is a flowchart showing the procedure of the sample dispensing control process.

The sample dispensing control process will now be described in detail. FIG. 13 is a flowchart showing the procedure of the sample dispensing control process. First, the CPU 301 controls the dispensing unit stepping motor unit 312 to position the pipette 21c of the first sample dispensing unit 21 immediately above the sample container 61 of the sample aspirating position 53 of the transport region of the transport path 51 or to position the pipette 22c of the second sample dispensing unit 22 immediately above the cuvette at the sample aspirating position 19 of the cuvette table 15 (step S501).

Then, the CPU 301 controls the dispensing unit stepping motor unit 312 to lower the pipette 21c of the first sample dispensing unit 21 or the pipette 22c of the second sample dispensing unit 22 at the first speed (step S502). The CPU 301 monitors the output signal from the dispensing unit rotary encoder unit 322, and determines whether or not the pipette reached the fixed speed switching height stored in the hard disc 304 (step S503). If the pipette has not reached the speed switching height (NO in step S503), the CPU 301 repeats the process of step S503 until the pipette reaches the speed switching height. The fixed speed switching height stored in the hard disc 304 in step S503 is set so as to be a sufficiently distant position even from the highest liquid surface of the reagent accommodated in the sample container.

If the pipette reached the speed switching height (YES in step S503), the CPU 301 controls the dispensing unit stepping motor unit 312 to lower the pipette 21c of the first sample dispensing unit 21 or the pipette 22c of the second sample dispensing unit 22 at the second speed slower than the first speed (step S504). The CPU 301 further monitors the output signal from the liquid surface sensor unit 323, and determines whether or not the distal end of the pipette is contacting the liquid surface (step S505). If the distal end of the pipette is not contacting the liquid surface (NO in step S505), the CPU 301 repeats the process of step S505 until the distal end of the pipette contacts the liquid surface.

If the distal end of the pipette is contacting the liquid surface (YES in step S505), the CPU 301 controls the dispensing unit stepping motor unit 312 so as to further lower the pipette to the depth corresponding to the dispensing amount of the sample (step S506), and thereafter causes the pipette to aspirate the sample (step S507). After the aspiration of the sample is completed, the CPU 301 controls the dispensing unit stepping motor unit 312 to move the pipette 21c of the first sample dispensing unit 21 to the cuvette at the sample discharging position 18 or to move the pipette 22c of the second sample dispensing unit 22 to the cuvette held at the cuvette transport unit 32 (step S508). The CPU 301 then causes the pipette 21c of the first sample dispensing unit 21 or the pipette 22c of the second sample dispensing unit 22 to discharge the sample to the cuvette (step S509), and terminates the process.

Figure 14:
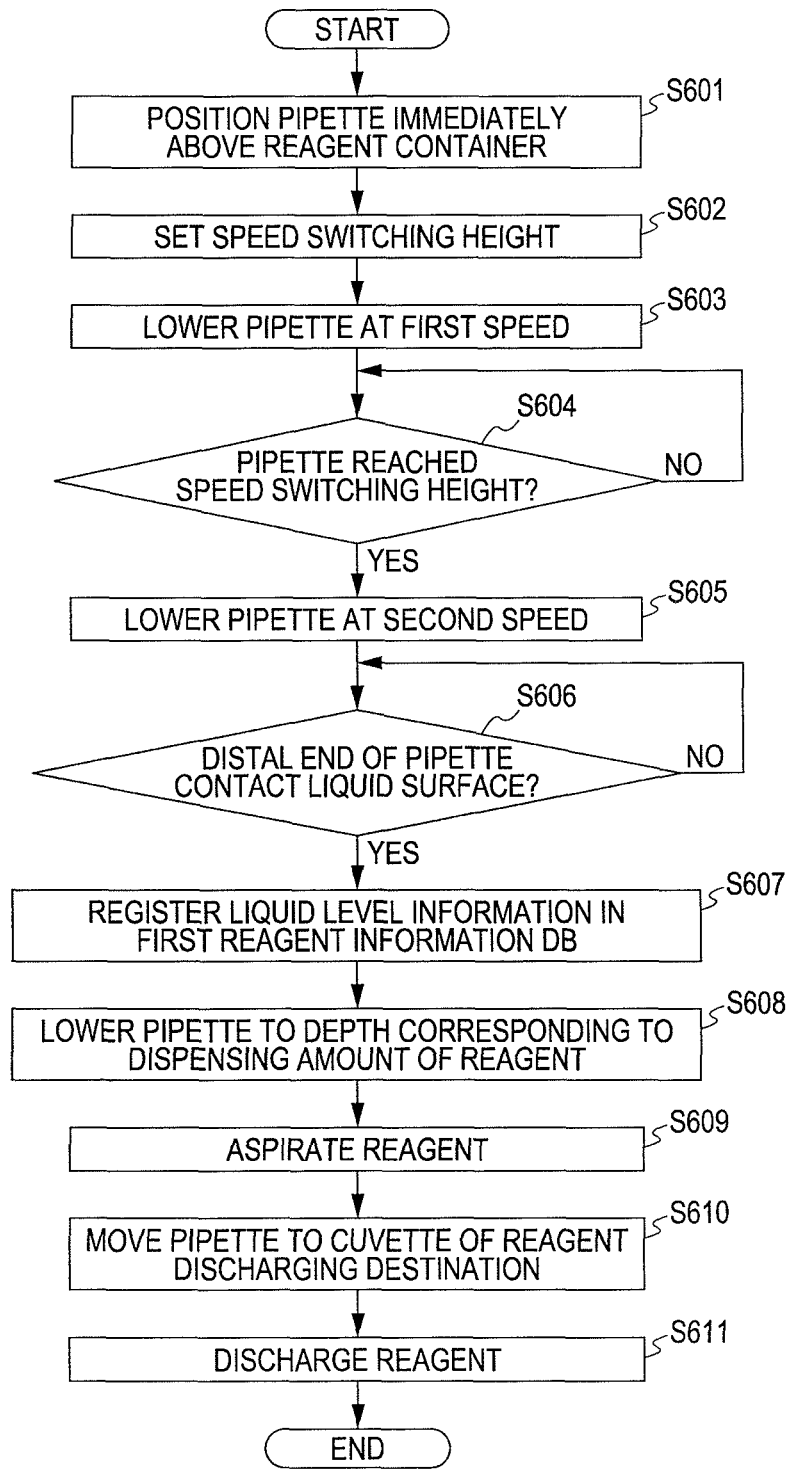
FIG. 14 is a flowchart showing the procedure of the reagent dispensing control process.

The reagent dispensing control process will now be described in detail. FIG. 14 is a flowchart showing the procedure of the reagent dispensing control process. First, the CPU 301 controls the reagent table stepping motor unit 311 and the dispensing unit stepping motor unit 312 to position the pipette 23c of the first reagent dispensing unit 23, the pipette 24c of the second reagent dispensing unit 24, or the pipette 25c of the third reagent dispensing unit 25 immediately above the reagent container accommodating the reagent to be aspirated (step S601).

The CPU 301 then monitors the output signal from the dispensing unit rotary encoder unit 322, reads out the liquid level information of the reagent to be aspirated stored in the first reagent information database 500, and sets the height on the upper side by a predetermined distance from the liquid level of the relevant reagent as the speed switching height (step S602). The CPU 301 controls the dispensing unit stepping motor unit 312 to lower the pipette 23c of the first reagent dispensing unit 23, the pipette 24c of the second reagent dispensing unit 24, or the pipette 25c of the third reagent dispensing unit 25 at the first speed (step S603), and determines whether or not the pipette reached the speed switching height set in step S602 (step S604). If the pipette has not reached the speed switching height (NO in step S604), the CPU 301 repeats the process of step S604 until the pipette reaches the speed switching height. The speed switching height set in step S602 is set to a position closer to the liquid surface than the fixed speed switching height stored in the hard disc 304 in step S404.

If the pipette reached the speed switching height (YES in step S604), the CPU 301 controls the dispensing unit stepping motor unit 312, and lowers the pipette 23c of the first reagent dispensing unit 23, the pipette 24c of the second reagent dispensing unit 24, or the pipette 25c of the third reagent dispensing unit 25 at the second speed slower than the first speed (step S605). The CPU 301 further monitors the output signal from the liquid surface sensor unit 323, and determines whether or not the distal end of the pipette is contacting the liquid surface (step S606). If the distal end of the pipette is not contacting the liquid surface (NO in step S606), the CPU 301 repeats the process of step S606 until the distal end of the pipette contacts the liquid surface.

If the distal end of the pipette is contacting the liquid surface (YES in step S606), the CPU 301 stores the result (value reflecting the liquid level after reagent aspiration) of adding the value corresponding to the reagent aspiration amount to the count value (value reflecting the liquid level at the relevant time point) of the rotary encoder corresponding to the pipette of when the distal end of the pipette contacts the liquid surface in the record corresponding to the reagent container of the first reagent information table as the liquid level information by the output signal from the dispensing unit rotary encoder unit 322 (step S607).

The CPU 301 then controls the dispensing unit stepping motor unit 312 to further lower the pipette to the depth corresponding to the dispensing amount of the reagent (step S608), and thereafter causes the pipette to aspirate the reagent (step S609). After the aspiration of the reagent is completed, the CPU 301 controls the dispensing unit stepping motor unit 312 to move the pipette 23c of the first reagent dispensing unit 23, the pipette 24c of the second reagent dispensing unit 24, or the pipette 25c of the third reagent dispensing unit 25 to the target cuvette (step S610). The CPU 301 further causes the pipette 23c of the first reagent dispensing unit 23, the pipette 24c of the second reagent dispensing unit 24, or the pipette 25c of the third reagent dispensing unit 25 to discharge the reagent to the cuvette (step S611), and terminates the process.

According to the configuration described above, the sample analyzer 1 according to the present embodiment acquires the accurate liquid level of the reagent when dispensing the reagent even immediately after the startup of the sample analyzer 1 or after replacement or addition of the reagent, and can lower the aspirating tube to the position close to the liquid surface at high speed. Thus, the reagent dispensing operation can be efficiently carried out. Furthermore, the entire operation of the sample analyzer 1 can be efficiently carried out since the initial liquid level detection operation is carried out in parallel with other operations such as sample dispensing operation and warming operation.

Other Embodiments

In the above described embodiment, a configuration of executing the initial liquid level detection operation only on the reagent corresponding to the measurement item contained in the measurement order received by the sample analyzer 1 of the reagents not used in the sample measurement after the sample analyzer 1 is started up has been described, but this is not the sole case. The initial liquid level detection operation may be executed on all the reagents not used in the sample measurement after the sample analyzer 1 is started up.

In the above described embodiment, a configuration of executing the initial liquid level detection operation after the measurement device 2 of the sample analyzer 1 starts the sample measurement operation has been described, but this is not the sole case. The initial liquid level detection operation may be incorporated in the initial operation of the measurement device 2, or the initial liquid level detection operation may be executed when the measurement device 2 is in the standby state capable of starting the measurement of the sample.

In the above described embodiment, the lowering speed to the speed switching height of the pipette 21c of the first sample dispensing unit 21 and the pipette 22c of the second sample dispensing unit 22 in the sample dispensing operation, and the lowering speed to the speed switching height of the pipette 23c of the first reagent dispensing unit 23, the pipette 24c of the second reagent dispensing unit 24, and the pipette 25c of the third reagent dispensing unit 25 in the reagent dispensing operation are both set to the first speed, but this is not the sole case. The lowering speed to the speed switching height of the pipette 21c of the first sample dispensing unit 21 and the pipette 22c of the second sample dispensing unit 22 in the sample dispensing operation may be a third speed different from the first speed. The lowering speed to the lower side than the speed switching height of the pipette 21c of the first sample dispensing unit 21 and the pipette 22c of the second sample dispensing unit 22 in the sample dispensing operation, and the lowering speed to the lower side than the speed switching height of the pipette 23c of the first reagent dispensing unit 23, the pipette 24c of the second reagent dispensing unit 24, and the pipette 25c of the third reagent dispensing unit 25 in the reagent dispensing operation are both set to the second speed, but this is not the sole case. The lowering speed to the lower side than the speed switching height of the pipette 21c of the first sample dispensing unit 21 and the pipette 22c of the second sample dispensing unit 22 in the sample dispensing operation may be a fourth speed different from the second speed. In this case, however, the efficient sample dispensing operation cannot be carried out unless the fourth speed is a speed slower than the third speed.

In the above described embodiment, a configuration in which the liquid level information indicating the liquid level of the reagent is stored in the first reagent information database 500, the height on the upper side of the liquid level indicated by the liquid level information by a predetermined distance is set as the speed switching height, and the lowering speed of the pipette is switched at the speed switching height has been described, but this is not the sole case. The speed switching height may be obtained from the liquid level detected in the initial liquid level detecting operation or the reagent dispensing operation, the speed switching height may be stored in the first reagent information database 500, and the speed switching height may be read from the first reagent information database 500 to switch the lowering speed of the pipette at the speed switching height in the reagent dispensing operation of next time. Furthermore, the liquid level information indicating the liquid level of the reagent when the liquid surface is detected in the reagent dispensing operation of the previous time may be stored in the first reagent information database, the liquid level indicated by the liquid level information may be set to the speed switching height, and the lowering speed of the pipette may be switched at the relevant speed switching height.

In the above described embodiment, a configuration in which the lowering speed of the pipette is changed in two stages in the sample dispensing operation and the reagent dispensing operation has been described, but this is not the sole case. For instance, a configuration of switching the speed in multi-stages of three or more stages may be adopted so as to lowering the pipette at the first speed at the initial stage of lowering of the pipette, lower the pipette at the second speed slower than the first speed at the intermediate stage of lowering of the pipette, and lowering the pipette at the third speed slower than the second speed at the last stage of lowering of the pipette, or a configuration of smoothly changing the lowering speed of the pipette from the first speed to the second speed may be adopted.

In the above described embodiment, a configuration of detecting that the distal end of the pipette contacted the liquid surface using the contact type liquid surface detection sensor has been adopted, but this is not the sole case. A configuration of detecting the liquid level using the non-contact type liquid surface sensor such as ultrasonic wave type may be adopted.

In the above described embodiment, a configuration in which the sample analyzer 1 separately includes the measurement device 2 for measuring the sample and the information processing device 3 for data processing the measurement result obtained by the measurement device 2 and obtaining the analysis result has been adopted, but this is not the sole case. The sample analyzer 1 having a configuration in which both functions of the measurement device 2 and the information processing device 3 are arranged in one housing may be adopted. In this case, the processes executed by the CPU 301 of the measurement device 2 and the CPU 401 of the information processing device 3 may be executed by one CPU.

In the above described embodiment, the sample analyzer 1 is a blood coagulation measurement device, but is not limited thereto. A configuration of detecting the liquid level of the reagent by the initial liquid level detecting operation, storing the information related to the liquid level, and lowering the pipette while switching speed based on the stored liquid level when dispensing the reagent may be adopted in a sample analyzer other than the blood coagulation measurement device such as a blood cell counting device, an immune analyzer, a urine formed element analyzer, or a urine qualitative analyzer.

In the above described embodiment, an example where the liquid level detection operation by the first reagent dispensing unit 23, the liquid level detection operation by the second reagent dispensing unit 24, the liquid level detection operation by the third reagent dispensing unit 25, the primary dispensing operation for the sample of sample number 1, and the like are executed in parallel has been described as an example of a schedule for sample measurement, but this is not the sole case. For instance, the dispensing of the reagent by the second reagent dispensing unit 24 may be executed while executing the liquid level detection operation by the first reagent dispensing unit 23. Furthermore, the optical measurement may be executed while executing the liquid level detection operation by the first reagent dispensing unit 23.

In the above described embodiment, a configuration in which the liquid level of the reagent acquired by the initial liquid level detection operation when dispensing the reagent is used to lower the aspirating tube at high speed up to the position close to the liquid surface and perform the reagent dispensing operation has been described, but this is not the sole case. The liquid level of the sample acquired by executing the initial liquid level detection operation on the sample may be used to lower the aspirating tube at high speed up to the position close to the liquid surface and perform the sample dispensing operation.

What is claimed is:

1. A sample analyzer comprising:
a liquid aspirating unit that includes an aspirating tube configured to aspirate a liquid from a container for a sample analysis and an actuator configured to move the aspirating tube in an up direction and a down direction;
a liquid surface detector, the liquid surface detector configured to detect a level of a liquid surface in the container;
a memory for storing liquid level information indicating the level of the liquid surface; and
a controller configured to determine whether the liquid level information is stored in the memory,
wherein, in response to determining that the liquid level information is stored in the memory, the controller is further configured to control a speed for lowering the aspirating tube with respect to the liquid surface in the container by the actuator, wherein the speed for lowering the aspirating tube is based on the liquid level information stored in the memory, and control the liquid aspirating unit to aspirate the liquid from the container with the aspirating tube, and
wherein, in response to determining that the liquid level information is not stored in the memory, the controller is further configured to control the liquid aspirating unit to, without aspirating the liquid, lower the aspirating tube, control the liquid surface detector to execute a liquid surface detection of the liquid surface in the container, control the liquid aspirating unit to raise the aspirating tube, and store corresponding liquid level information based on the liquid surface detection in the memory,
wherein the controller is further configured to:
if the liquid level information is not stored in the memory, control the actuator to lower the aspirating tube at a first speed to a predetermined height and to lower the aspirating tube at a second speed slower than the first speed from the predetermined height to execute the liquid surface detection with respect to the liquid in the container, and
if the liquid level information is stored in the memory, acquire, based on the liquid level information stored in the memory, a speed switching height at which a lowering speed of the aspirating tube is switched, and control the actuator to lower the aspirating tube at the first speed to the acquired speed switching height and to lower the aspirating tube at a third speed slower than the first speed from the speed switching height to cause the aspirating tube to aspirate the liquid from the container.

2. The sample analyzer according to claim 1, wherein the liquid surface detector detects a contact of the aspirating tube with the liquid surface in the container.

3. The sample analyzer according to claim 2, wherein the aspirating tube includes a first aspirating tube and a second aspirating tube,
the actuator includes a first actuator for moving the first aspirating tube in the up direction and the down direction and a second actuator for moving the second aspirating tube in the up direction and the down direction, and
if a second liquid level information of another container different from the liquid level of the container is stored in the memory, the controller is further configured to control the liquid aspirating unit to execute at least one part of an aspirating operation for aspirating a liquid from the another container by lowering the second aspirating tube while controlling the liquid surface detector to execute the liquid surface detection with respect to the liquid in the container.

4. The sample analyzer according to claim 1, comprising an operation mechanism for executing another operation for analyzing the sample, different from an operation for the liquid surface detection, wherein
the controller is further configured to control the operation mechanism to execute at least one part of the other operation while executing the liquid surface detection with respect to the liquid in the container.

5. The sample analyzer according to claim 4, wherein the operation mechanism is configured to execute as the other operation at least one of an operation of dispensing a sample, an operation of transporting a container accommodating the sample, an operation of warming the sample, an operation of dispensing a reagent, and an operation of measuring the sample mixed with the reagent.

6. The sample analyzer according to claim 1, wherein the container is a reagent container of a plurality of reagent containers,
the sample analyzer further comprises a reagent container holder for holding the plurality of reagent containers,
the memory is configured to store reagent information indicating a type of reagent in each of the plurality of reagent containers, and
the controller is further configured to identify the container based on the reagent information.

7. The sample analyzer according to claim 6, wherein the liquid level information comprises information indicating a specific liquid level for each of the plurality of reagent containers, and
the controller comprises:
a first controller configured to identify the container based on the reagent information; and
a second controller configured to control the detector to execute the liquid surface detection with respect to the reagent in the container.

8. The sample analyzer according to claim 1, further comprising:
a reagent container holder for holding the container;
a cover for covering the reagent container holder; and
an open/close detector for detecting an opening and a closing of the cover, wherein
the controller is further configured to, in response to determining the liquid level is not stored in the memory, control the liquid surface detector to execute the liquid surface detection when the closing of the cover is detected by the open/close detector.

9. The sample analyzer according to claim 8, wherein the container is a reagent container of a plurality of reagent containers,
the reagent container holder is configured to hold the plurality of reagent containers,
the cover is configured to be openable and closable at one part of the reagent container holder, and the controller is further configured to, in response to determining the liquid level is not stored in the memory, control the liquid surface detector to execute the liquid surface detection when the closing of the cover is detected by the open/close detector.

10. The sample analyzer according to claim 8, further comprising
an opening prohibiting mechanism for prohibiting opening of the cover, wherein
the controller is further configured to, in response to determining the liquid level is not stored in the memory, control the liquid surface detector to execute the liquid surface detection while opening of the cover is prohibited by the opening prohibiting mechanism.

* * * * *